United States Patent [19]

Bryans et al.

[11] Patent Number: 5,852,018
[45] Date of Patent: Dec. 22, 1998

[54] PHARMACEUTICAL PIPERAZINE COMPOUNDS

[75] Inventors: Justin Stephen Bryans; Christopher John Latham, both of Slough, United Kingdom; Stephen James Brocchini, Highland Park, N.J.

[73] Assignee: Xenova Limited, United Kingdom

[21] Appl. No.: 693,171

[22] PCT Filed: Feb. 14, 1995

[86] PCT No.: PCT/GB95/00300

§ 371 Date: Nov. 4, 1996

§ 102(e) Date: Nov. 4, 1996

[87] PCT Pub. No.: WO95/21830

PCT Pub. Date: Aug. 17, 1995

(Under 37 CFR 1.47)

[30] Foreign Application Priority Data

Feb. 14, 1994 [GB] United Kingdom .................. 9402809

[51] Int. Cl.⁶ .................... A61K 31/495; C07D 241/08; C07D 403/06
[52] U.S. Cl. .................... 514/252; 514/183; 514/250; 514/253; 514/255; 540/480; 544/344; 544/360; 544/372; 544/373; 544/374; 544/385
[58] Field of Search .................... 544/385, 405, 544/408, 360, 372–374; 514/252, 253, 255

[56] References Cited

FOREIGN PATENT DOCUMENTS

C 621862 11/1935 Germany .
WO A 94 04513 3/1994 WIPO .

OTHER PUBLICATIONS

Marcuccio et al, *Aust. J. Chem.* 37 pp. 2397–2402, 1984.
Ashworth et al, *Chemical Abstracts*, vol. 125, No. 168024 (1996).
Kamei et al, *J. Antibiotics,* vol. XLlll, pp. 1018–1020 (1990).
Ogasawara et al, *J. Antibiotics* vol. 45, pp. 129–132 (1992).
Shin et al, *Chemistry Letters* pp. 1453–1456 (1986).
Wu et al, *Chemical Abstracts,* vol. 113, No. 17408 (1990).
Yokoi et al, *J. Antibiotics* vol. XLl, pp. 494–501 (1988).
Bellamy et al, *Cancer Investigation* 8 (5), pp. 547–562 (1990).
Chemical Abstracts, vol. 69, No. 28, 1968, Columbus, Ohio, US; abstract No. 96654q, R.F.C. Brown et al. 'Synthetic Approaches To Mycelinamamide.' p. 9051.
Bulletin Of The Chemical Society Of Japan, vol. 59, No. 12, Dec. 1986, Tokyo JP pp. 3917–3923, Chung–Gi Shin et al. 'Convenient Synthesis Of 3–Aminocourmarin' see p. 3919–p. 3921; example 8C.

*Primary Examiner*—Emily Bernhardt
*Attorney, Agent, or Firm*—Nixon & Vanderhye

[57] ABSTRACT

Piperazine derivatives of formula (A):

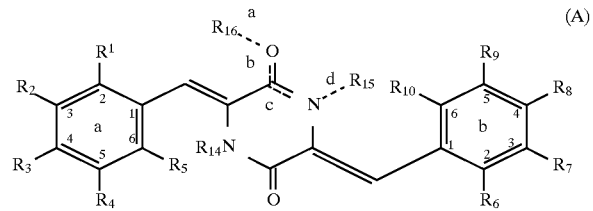

wherein _____ denotes an optional bond, provided that either __a__ and __c__ are both bonds and __b__ and __d__ are not bonds, or __b__ and __d__ are both bonds and __a__ and __c__ are not bonds; each of $R_{14}$ and $R_{15}$ is independently selected from hydrogen and $C_1$–$C_6$ alkyl which is unsubstituted or substituted by an organic functional group; and each of $R_1$ to $R_{10}$, which may be the same or different, is independently hydrogen or an organic functional group; and the pharmaceutically acceptable salts and esters thereof have utility as modulators of multiple drug resistance (MDR).

10 Claims, No Drawings

PHARMACEUTICAL PIPERAZINE COMPOUNDS

The present invention relates to compounds useful as modulators of multiple drug resistance (MDR), to their preparation and to pharmaceutical and veterinary compositions containing them.

The resistance of tumours to treatment with certain cytotoxic agents is an obstacle to the successful chemotherapeutic treatment of cancer patients. A tumour may acquire resistance to a cytotoxic agent used in a previous treatment. A tumour may also manifest intrinsic resistance, or cross-resistance, to a cytotoxic agent to which it has not previously been exposed, that agent being unrelated by structure or mechanism of action to any agent used in previous treatments of the tumour.

Analogously, certain pathogens may acquire resistance to pharmaceutical agents used in previous treatments of the diseases or disorders to which those pathogens give rise. Pathogens may also manifest intrinsic resistance, or cross resistance, to pharmaceutical agents to which they have not previously been exposed. Examples of this effect include multi-drug resistant forms of malaria, tuberculosis, leishmaniasis and amoebic dysentery.

The above phenomena are referred to collectively as multi-drug resistance (MDR). As discussed more fully later on, a plasma membrane glycoprotein (P-gp) is implicated in the mechanism which underlies MDR. P-gp has drug binding properties. Certain agents which have the capacity to modulate MDR may therefore also be useful in facilitating the delivery of drugs across the blood-brain barrier and in treating AIDS and AIDS-related complex.

Disadvantages of drugs which have so far been used to modulate MDR, termed resistance modifying agents or RMAs, are that they frequently possess a poor pharmacokinetic profile and/or are toxic at the concentrations required for MDR modulation.

It has now been found that a series of piperazine derivatives have activity as modulators of multiple drug resistance. The present invention therefore provides a piperazine of formula (A):

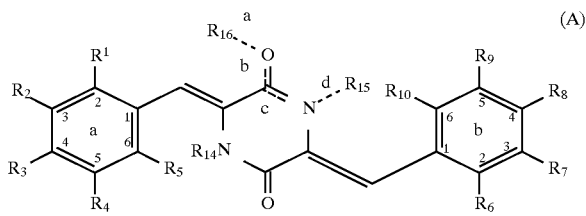

wherein _____ denotes an optional bond, provided that either ___$a$___ and ___$c$___ are both bonds and ___$b$___ and ___$d$___ are not bonds, or ___$b$___ and ___$d$___ are both bonds and ___$a$___ and ___$c$___ are not bonds; each of $R_{14}$ and $R_{15}$ is independently selected from hydrogen and $C_1$-$C_6$ alkyl which is unsubstituted or substituted by a group selected from halogen, optionally substituted phenyl, optionally substituted $C_1$-$C_6$ alkenyl, cyano, hydroxy, —OC(O)$R^{11}$, —N($R^{11}R^{12}$) —CON($R^{11}R^{12}$), —COOR$^{11}$, succinimido, phthalimido, and

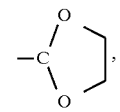

provided that, when ___$b$___ and ___$d$___ are both bonds at least one of $R_{14}$ and $R_{15}$ is $C_1$-$C_6$ alkyl substituted as defined above; or $R_{14}$ forms a —CH$_2$— linkage to ring a, thereby completing a 6-membered N-containing heterocycle with the nitrogen to which it is attached; $R_{16}$ is $C_1$-$C_6$ alkyl unsubstituted or substituted either as defined above for $R_{14}$ and $R_{15}$ or substituted by a pyridyl group; and each of $R_1$ to $R_{10}$, which may be the same or different, is independently selected from hydrogen, $C_1$-$C_6$ alkyl unsubstituted or substituted by one or more halogen atoms, $C_1$-$C_6$ alkoxy, $C_1$-$C_6$ alkylthio, halogen, hydroxy, nitro, optionally substituted phenyl, cyano, —CH$_2$OH, —CH$_2$COOH, —CO$_2$R$^{11}$, —NHCOR$^{11}$, —NHSO$_2$R$^{13}$, —SO$_2$R$^{13}$, —CON(R$^{11}$R$^{12}$), —SOR$^{13}$, —SO$_2$N(R$^{11}$R$^{12}$), —N(R$^{11}$R$^{12}$), —O(CH$_2$)$_n$N(R$^{11}$R$^{12}$), —O(CH$_2$)$_n$CO$_2$R$^{11}$, —OCOR$^{11}$, —CH$_2$OCOR$^{11}$, —CH$_2$NHCOR$^{11}$, —CH$_2$NHCOOR$^{13}$, —CH$_2$SR$^{11}$, —CH$_2$SCOR$^{11}$, —CH$_2$S(O)$_m$R$^{13}$ wherein m is 1 or 2, —CH$_2$NHCO(CH$_2$)$_n$CO$_2$R$^{11}$, —N(R$^{11}$)COR$^{12}$, —NHCOCF$_3$, —NHCO(CH$_2$)$_n$CO$_2$R$^{11}$, —NHCO(CH$_2$)$_n$OCOR$^{11}$ and —NHCO(CH$_2$)$_n$OR$^{11}$;

wherein n is 0 or is an integer of from 1 to 6, each of R$^{11}$ and R$^{12}$ is independently H or $C_1$-$C_6$ alkyl or, when R$^{11}$ and R$^{12}$ are attached to the same nitrogen atom, they may alternatively form with the nitrogen atom a saturated five or six-membered heterocyclic ring; and R$^{13}$ is $C_1$-$C_6$ alkyl; or a pharmaceutically acceptable salt or ester thereof.

In one embodiment the compound is of the following formula (Aa):

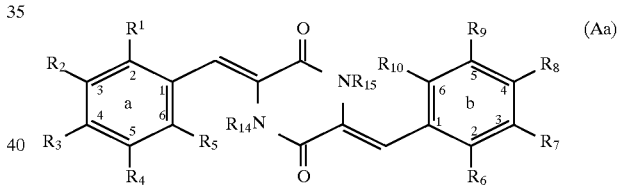

wherein each of $R_1$ to $R_{10}$, $R_{14}$ and $R_{15}$ is as defined above.

In another embodiment the compound is of the following formula (Ab):

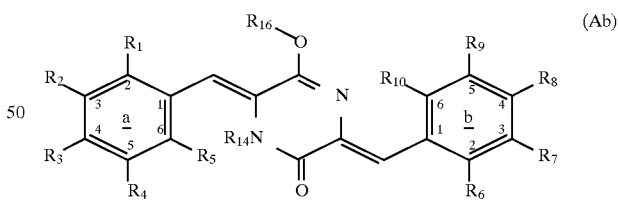

wherein each of $R_1$ to $R_{10}$, $R_{14}$ and $R_{16}$ is as defined above.

The numerals 1 to 10 denote ring positions on the phenyl groups in formula A. The letters a and b refer to the two phenyl rings themselves.

When ring a or b is substituted phenyl, the benzene ring may be substituted at any of the ortho, meta and para positions by one or more substituents, for example one, two or three substituents, which may be the same or different, independently selected from the groups specified above for $R_1$ to $R_{10}$ other than hydrogen.

A $C_1$-$C_6$ alkyl group may be linear or branched, or may comprise a cycloalkyl group. A $C_1$-$C_6$ alkyl group is typically a $C_1$-$C_4$ alkyl group, for example a methyl, ethyl, propyl, i-propyl, n-butyl, sec-butyl, tert-butyl or cyclopropylmethyl group. A halogen is, for example, fluorine, chlorine, bromine or iodine. A $C_1$–$C_6$ alkyl group substituted by halogen may be substituted by 1, 2 or 3 halogen atoms. It may be a perhaloalkyl group, for example trifluoromethyl.

A $C_1$–$C_6$ alkenyl group is typically a $C_1$–$C_4$ alkenyl group, for instance —$CH_2$—$CH$=$CH_2$ or —$CH_2$—$CH$=$CHCH_3$.

A $C_1$–$C_6$ alkoxy group is typically a $C_1$–$C_4$ alkoxy group, for example a methoxy, ethoxy, propoxy, i-propoxy, n-butoxy, sec-butoxy or tert-butoxy group. A $C_1$–$C_6$ alkylthio group is typically a $C_1$–$C_4$ alkylthio group, for example methylthio, ethylthio, propylthio, i-propylthio, n-butylthio, sec-butylthio or tert-butylthio.

When $R^{11}$ and $R^{12}$ form a heterocyclic group together with the nitrogen atom to which they are attached, it is, for example, an N,N-tetramethylene group.

In compounds of formula A, Aa or Ab free rotation may occur at room temperature about the single bonds connecting rings a and b to the double bonds at positions 3 and 6 of the 2,5-piperazinedione ring. Positions 2 and 6, and positions 3 and 5, in both rings a and b can therefore be considered as equivalent. As a consequence the following pairs of substituents can be viewed as interchangeable: $R_1$ and $R_5$; $R_2$ and $R_4$; $R_6$ and $R_{10}$; and $R_7$ and $R_9$.

When in formula A ___b___ and ___d___ are both bonds, or in formula Aa, one of $R_{14}$ and $R_{15}$ is $C_1$–$C_6$ alkyl substituted as defined above. The other may be hydrogen or $C_1$–$C_6$ alkyl, either unsubstituted or substituted as defined above. When $R_{14}$ and $R_{15}$ are both substituted $C_1$–$C_6$ alkyl they may be the same or different. Preferred substituted $C_1$–$C_6$ alkyl groups for $R_{14}$ and $R_{15}$ are $C_1$–$C_6$ alkyl groups substituted by halogen, phenyl, 4-nitrophenyl, —COOH, —COOMe, —$CH_2$—CH=CH—$CH_3$, —$CH_2$—CH=$CH_2$, —$CH_2$CH=CH—$CH_2$X, cyano, —OC(O)$CH_3$—C(O)NMe, —C(O)NHMe, —C(O)$NH_2$,

and succinimido, wherein X is halogen, particularly bromine. For example, $R_{14}$ is H or $C_1$–$C_6$ alkyl and $R_{15}$ is a preferred substituted $C_1$–$C_6$ alkyl group specified above. In one embodiment $R_{14}$ is H, Me, or cyclopropylmethyl and $R_{15}$ is a preferred substituted $C_1$–$C_6$ alkyl group specified above.

When in formula A ___a___ and ___c___ are both bonds, or in formula Ab, $R_{14}$ is hydrogen, or unsubstituted or substituted $C_1$–$C_6$ alkyl as defined above, then $R_{16}$ is unsubstituted or substituted $C_1$–$C_6$ alkyl as defined above. Typically at least one of $R_{14}$ and $R_{16}$ is $C_1$–$C_6$ alkyl substituted as defined above, for instance $R_{16}$ is $C_1$–$C_6$ alkyl substituted as defined above and $R_{14}$ is unsubstituted alkyl, for instance Me.

Preferably one of rings a and b is unsubstituted or is mono-substituted whilst the other ring is unsubstituted or is substituted at one or more of positions 2 to 6. The ring which is mono-substituted may carry the substituent at any one of positions 2 to 6, for instance position 3 or 4, especially position 4. Thus for instance, when ring b is mono-substituted, one of $R_6$ to $R_{10}$ is other than hydrogen, preferably $R_7$ or $R_8$, especially $R_8$. When ring a is mono-substituted one of $R_1$ to $R_5$ is other than hydrogen, preferably $R_2$ or $R_3$, especially $R_3$. When one of rings a and b is mono-substituted the substituent $R_1$ to $R_5$, or $R_6$ to $R_{10}$ respectively, is preferably selected from a halogen, for instance fluorine; an alkoxy group, for instance OMe; and an acetamido group —NHAc in which Ac denotes acetyl.

When one of rings a and b is unsubstituted, or is mono-substituted as described in the above paragraph, the other ring may bear any desired substitution pattern. For instance, the other ring may be unsubstituted or may be mono-, di- or tri-substituted at any of positions 2 to 6.

The said other ring may, for instance, be mono-substituted at any of positions 2 to 6. It may also be 2,3-, 2,4-, 2,5-, 2,6-, 3,4- or 3,5-disubstituted, or 2,3,4-, 2,3,5-, 2,3,6- or 3,4,5-trisubstituted. Thus, when the said other ring is a and is mono-substituted, four of $R_1$ to $R_5$ are hydrogen and one is other than hydrogen. When the said other ring is ring a and is disubstituted, three of $R_1$ to $R_5$ are hydrogen and two are other than hydrogen. For example $R_1$ and $R_2$, or $R_1$ and $R_3$, or $R_1$ and $R_4$, or $R_1$ and $R_5$, or $R_2$ and $R_3$, or $R_2$ and $R_4$ are other than hydrogen whilst, in each case, the other three of $R_1$ to $R_5$ are hydrogen.

When the said other ring is ring a and is trisubstituted, two of $R_1$ to $R_5$ are hydrogen and three are other than hydrogen. For example, $R_1$, $R_2$ and $R_3$, or $R_1$, $R_2$ and $R_4$, or $R_1$, $R_2$ and $R_5$, or $R_2$, $R_3$ and $R_4$ are other than hydrogen whilst, in each case, the other two of $R_1$ to $R_5$ are hydrogen.

When the said ring is b and is mono-substituted, four of $R_6$ to $R_{10}$, are hydrogen and one is other than hydrogen. When the said other ring is b and is di-substituted, three of $R_6$ to $R_{10}$ are hydrogen and two are other than hydrogen. For example $R_6$ and $R_7$, or $R_6$ and $R_8$, or $R_6$ and $R_9$, or $R_6$ and $R_{10}$, or $R_7$ and $R_8$, or $R_7$ and $R_9$, are other than hydrogen whilst, in each case, the other three of $R_6$ to $R_{10}$ are hydrogen. When the said other ring is b and is trisubstituted, two of $R_6$ to $R_{10}$ are hydrogen and three are other than hydrogen. For example $R_6$, $R_7$ and $R_8$, or $R_6$, $R_7$ and $R_9$, or $R_6$, $R_7$ and $R_{10}$, or $R_7$, $R_8$ and $R_9$ are other than hydrogen whilst, in each case, the other two of $R_6$ to $R_{10}$ are hydrogen.

In a preferred series of compounds of formula A each of $R_1$ to $R_{10}$ is hydrogen. In another preferred series of compounds, one of $R_6$ to $R_{10}$ is selected from hydroxy, alkoxy, $NHCOR^{11}$, —$CO_2R^{11}$, —$N(R^{11}R^{12})$, —$O(CH_2)_nN(R^{11}R^{12})$, —$SO_2R^{13}$, —$CON(R^{11}R^{12})$, $NO_2$, —$SO_2N(R^{11}R^{12})$, —$SOR^{13}$, —$N(R^{11})COR^{12}$ and halogen and the other four of $R_6$ to $R_{10}$ are H. Alkoxy may be, for instance, OMe or OBu$^n$. $NHCOR^{11}$ is typically —NHAc. $CO_2R^{11}$ is typically —COOH or —COOMe. $N(R^{11}R^{12})$ is typically $NMe_2$ or N,N-tetramethylene. —$CON(R^{11}R^{12})$ may be —$CONH_2$. $SO_2R^{13}$ is typically $SO_2Me$, $SO_2N(R^{11}$ $^{R12})$ is for example —$SO_2NMe_2$. $SOR^{13}$ may be SOMe and —$N(R^{11})COR^{12}$ may be —NMeCOBu$^t$. Halogen is typically F or Cl. Preferably $R_8$ is alkoxy, especially OMe or OBu$^n$; $NHCOR^{11}$, especially —NHAc; —$CO_2R^{11}$, especially —$CO_2H$ or —$CO_2Me$; —$CON(R^{11}R^{12})$ especially —$CONH_2$; $NO_2$; $N(R^{11}R^{12})$ especially $NMe_2$ or N,N-tetramethylene; —$SOR^{13}$ especially —SOMe; —$SO_2N(R^{11}R^{12})$ especially —$SO_2NMe_2$ or halogen, especially F or Cl; and each of $R_6$, $R_7$, $R_9$ and $R_{10}$, is H.

In the above-mentioned series of preferred compounds $R_1$ to $R_5$ are all hydrogen, or one or two of $R_1$ to $R_5$ are other than hydrogen whilst the others are hydrogen. For instance one of $R_1$, $R_2$ and $R_3$ is other than hydrogen. Alternatively $R_1$ and $R_3$, or $R_2$ and $R_3$, are other than hydrogen. Preferred values for the one or two of $R_1$ to $R_5$ which is or are other than hydrogen include alkoxy such as OMe or OBu$^n$, halogen such as Cl or F, hydroxy, —$N(R^{11}R^{12})$, —$CO_2R^{11}$, —$CH_2SCOR^{13}$, —$CH_2SR^{11}$, —$NHCOR^{11}$, —$O(CH^2)_nN(R^{11}$ $^{R12})$, —$O(CH_2)_nCO_2R^{11}$, —$CH_2NHCO(CH_2)_nCO_2R^{11}$, —$NHCOCH_2OR^{11}$, —$NHCOCH_2OCOR^{13}$, —$CH_2NHCOOR^{13}$ and $CF_3$.

In a yet further preferred series one of $R_3$ and $R_8$ is alkoxy and the remainder of $R_1$ to $R_{10}$ are all H.

Particularly preferred compounds are those wherein $R_6$, $R_7$, $R_9$ and $R_{10}$ are each H, $R_8$ is selected from H, OMe —NHAc, —CO$_2$H, —CO$_2$Me, —COHN$_2$, NO$_2$, —NMe$_2$, N,N-tetramethylene, SO$_2$Me, —SOMe and —SO$_2$NMe$_2$ and each of $R_1$ to $R_5$ is as specified above. In these preferred compounds $R_1$ to $R^5$ are preferably each independently selected from H, halogen, hydroxy, $C_1$–$C_6$ alkoxy, nitro, —CH$_2$SCOR$^{13}$, —CH$_2$SR$_{11}$, —CO$_2$R$^{11}$, —OCOR$^{13}$, CF$_3$, —O(CH$_2$)$_n$N(R$^{11}$R$^{12}$), —O(CH$_2$)$_n$CO$_2$R$^{11}$, —CH$_2$NHCO (CH$_2$)$_n$CO$_2$R$^{11}$, —NHCO(CH$_2$)$_n$OR$^{11}$, —N(R$^{11}$R$^{12}$), —NHCO(CH$_2$)$_n$OCOR$^{11}$, —NHCO(CH$_2$)$_n$ $_{CO2}$R$^{11}$ and —CH$_2$NHCO$_2$R$^{13}$ or $R_1$ and $R_2$, $R_2$ and $R_3$, $R_3$ and $R_4$, or $R_4$ and $R_5$, form with the carbon atoms to which they are attached an optionally substituted benzene ring. Still more preferably, $R_1$ and $R_2$ are independently H, nitro or halogen, $R_3$ is H, hydroxy, —O(CH$_2$)$_n$N(R$^{11}$R$^{12}$), —OCOR$^{13}$, —O(CH$_2$)$_n$CO$_2$R$^{11}$, —CH$_2$NHCO(CH$_2$)$_n$CO$_2$R$^{11}$, $C_1$–$C_6$ alkoxy, —NHCO(CH$_2$)$_n$OR$^{11}$, —NHCO(CH$_2$)$_n$OCOR$^{11}$, —N(R$^{11}$R$^{12}$), —CH$_2$NHCO$_2$R$^{13}$, —CH$_2$SR$^{11}$ or —NHCOR$^{11}$; $R_4$ is H, halogen, $C_1$–$C_6$ alkoxy, —CH$_2$SCOR$^{13}$, —CH$_2$SR$^{11}$or —CO$_2$R$^{11}$; and $R_5$ is H, nitro or halogen.

In one embodiment $R^8$ is NHAc, each of $R_6$, $R_7$, $R_9$ and $R_{10}$, is H; $R_1$ is H or halogen such as Cl or F; $R_2$ is H, $R_3$ is halogen such as F or Cl, $C_1$–$C_6$ alkoxy such as OMe, —N(R$^{11}$R$^{12}$) such as NMe$_2$ or —NHCOOR$^{13}$ such as —NHCOOBu$^t$; $R_4$ is H and $R_5$ is halogen such as F, Cl, Br, or is CF$_3$.

In a further embodiment $R^8$ is OMe, each of $R_6$, $R_7$, $R_9$ and $R_{10}$ is H; $R^1$ is H, nitro or halogen such as Cl; $R^2$ is H; $R^3$ is H, hydroxy, —OCOR$^{13}$ such as OAc, —NHCO(CH$_2$)$_n$OCOR$^{11}$ such as —NHCOCH$_2$OAc or —NHCOCH$_2$OR$^{11}$ such as —NHCOCH$_2$OH; $R_4$ is H and $R_5$ is H or halogen such as F or Cl; or $R_2$ and $R_3$ form a benzene ring together with the carbon atoms to which they are attached.

In a further embodiment each of $R_1$, $R_6$, $R_7$, $R_8$, $R_9$ and $R_{10}$ is H; $R_2$ is H, —CH$_2$SCOR$^{13}$ such as —CH$_2$SAc or —CH$_2$SR$^{11}$ such as —CH$_2$SH; $R_3$ is —CH$_2$SR$^{11}$ such as —CH$_2$SMe, —CH$_2$SCOR$^{13}$ such as —CH$_2$SAc, —NHCO (CH$_2$)$_n$CO$_2$R$^{11}$ such as —NHCO(CH$_2$)$_3$CO$_2$Me, —O(CH$_2$)$_n$CO$_2$R$^{11}$ such as —O(CH$_2$)$_4$CO$_2$H, —O(CH$_2$)$_n$N(R$^{11}$R$^{12}$) such as —O(CH$_2$)$_3$NMe$_2$, or —N(R$^{11}$R$^{12}$) such as —NMe$_2$; and $R_4$ and $R_5$ are both H or both form, together with the carbon atoms to which they are attached, a benzene ring.

Certain diketopiperazines have been disclosed as having utility as bioactive agents. Yokoi et al in *J. Antibiotics* vol XLI No. 4, pp 494–501 (1988) describe structure-cytotoxicity relationship studies on a series of diketopiperazines related to neihumicin, a compound obtained from the micro-organism *Micromonospora neihuensis*. Kamei et al in J. Antibiotics vol XLIII No. 8, 1018–1020 disclose that two diketopiperazines, designated piperafizines A and B, have utility as potentiators of the cytotoxicity of vincristine.

Examples of specific compounds of the invention are as follows. The compound numbering is adhered to in the rest of the specification:

1824 (3Z,6Z)-3,6-Dibenzylidene-1-methyl-5-(3-phthalimidopropoxy)-3,6-dihydro-2-pyrazinone.
1826 (3Z,6Z)-3,6-Dibenzylidene-5-(3-butenyloxy)-1-methyl-3,6-dihydro-2-pyrazinone.
1827 (3Z,6Z)-3,6-Dibenzylidene-1-methyl-2-oxo-1,2,3,6-tetrahydro-5-pyrazinyloxyacetonitrile.
1823 (3Z,6Z)-3,6-Dibenzylidene-4-methyl-2,5-dioxo-1-piperazinylacetaldehyde ethylene acetal.
1822 (3Z,6Z)-3,6-Dibenzylidene-1-methyl-2-oxo-1,2,3,6-tetrahydro-5-pyrazinyloxyacetaldehyde ethylene acetal.
1818 (3Z,6Z)-5-(2-Acetoxyethoxy)-3,6-dibenzylidene-1-methyl-3,6-dihydro-2-pyrazinone.
1820 (3Z,6Z)-3,6-Dibenzylidene-1-methyl-5-(2-phenethoxy)-3,6-dihydro-2-pyrazinone.
1821 (3Z,6Z)-3,6-Dibenzylidene-5-isobutoxy-1-methyl-3,6-dihydro-2-pyrazinone.
1859 (3Z,6Z)-3,6-Dibenzylidene-5-(4-bromo-2-butenyloxy)-1-methyl-3,6-dihydro-2-pyrazinone.
1861 (3Z,6Z)-3,6-Dibenzylidene-5-(2-butenyloxy)-1-methyl-3,6-dihydro-2-pyrazinone.
1903 (3Z,6Z)-3,6-Dibenzylidene-1-methyl-5-(4-phthalimidobutoxy)-3,6-dihydro-2-pyrazinone.
1904 (3Z,6Z)-5-(4-Acetoxybutoxy)-3,6-dibenzylidene-1-methyl-3,6-dihydro-2-pyrazinone.
1905 (3Z,6Z)-3,6-Dibenzylidene-1-methyl-5-phthalimidomethoxy-3,6-dihydro-2-pyrazinone.
1902 (3Z,6Z)-3,6-Dibenzylidene-1-methyl-5-(2-phthalimidoethoxy)-3,6-dihydro-2-pyrazinone.
1901 (3Z,6Z)-3,6-Dibenzylidene-1-methyl-5-(4-pyridyl) methoxy-3,6-dihydro-2-pyrazinone.
1863 (3Z,6Z)-3,6-Dibenzylidene-5-(2-hydroxyethoxy)-1-methyl-3,6-dihydro-2-pyrazinone.
1864 (3Z,6Z)-5-Allyloxy-3,6-dibenzylidene-1-methyl-3,6-dihydro-2-pyrazinone.
1900 (3Z,6Z)-3,6-Dibenzylidene-5-(3-dimethylaminopropoxy)-1-methyl-3,6-dihydro-2-pyrazinone.
1819 (3Z,6Z)-3,6-Dibenzylidene-5-isopropoxy-1-methyl-3,6-dihydro-2-pyrazinone.
1801 (3Z,6Z)-3,6-Dibenzylidene-5-ethoxy-1-methyl-3,6-dihydro-2-pyrazinone.
1825 (3Z,6Z)-1-Allyl-3,6-dibenzylidene-4-methyl-2,5-piperazinedione.
1906 (3Z,6Z)-1,4-Dibenzyl-3,6-dibenzylidene-2,5-piperazinedione.
1936 (3Z,6Z)-3,6-Dibenzylidene-1-methyl-4-(3-nitrobenzylidene)-2,5-piperazinedione.
1817 (3Z,6Z)-1-(2-Acetoxyethyl)-3,6-dibenzylidene-4-methyl-2,5-piperazinedione.
1803 (3Z,6Z)-3,6-Dibenzylidene-1-(2-bromoethyl)-4-methyl-2,5-piperazinedione.
1939 (3Z,6Z)-3,6-Dibenzylidene-1-methyl-4-(4-nitrobenzylidene)-2,5-piperazinedione.
1486 Methyl (3Z,6Z)-3-benzylidene-6-(4-methoxybenzylidene)-2,5-dioxo-1-piperazinylacetate.
1614 N,N,-Dimethyl-(3Z,6Z)-3-benzylidene-6-(4-methoxybenzylidene)-2,5-dioxo-1-piperazinylacetamide.
1745 (3Z,6Z)-6-Benzylidene-5-cyclopropylmethoxy-3-(4-methoxybenzylidene)-1-methyl-3,6-dihydro-2-pyrazinone.
1780 (3Z,6Z)3,6-Dibenzylidene)-5-cyclohexylmethoxy-1-methyl-3,6-dihydro-2-pyrazinone.
1612 (3Z)-3-Benzylidene-1,4-dioxo-5(H)-piperazino(1,2-6) isoquinoline.
1527 N,N-Diethyl-(3Z,6Z)-6-benzylidene-3-(4-methoxybenzylidene)-2,5-dioxo-1-piperazinylacetamide.
1490 Methyl (3Z,6Z)-6-benzylidene-3-(4-methoxybenzylidene)-2,5-dioxo-1-piperazinylacetate.
1521 N,N-Tetramethylene-(3Z,6Z)-3-benzylidene-6-(4-methoxybenzylidene)-2,5-dioxo-1-piperazinylacetamide.
1526 N,N-Tetramethylene-(3Z,6Z)-6-benzylidene-3-(4-methoxybenzylidene)-2,5-dioxo-1-piperazinylacetamide.
1454 (3Z,6Z)-3-Benzylidene-1-cyclopropylmethyl-6-(4-methoxybenzylidene)-2,5-piperazinedione.
1779 (3Z,6Z)-1-Benzyl-3,6-dibenzylidene-4-methyl-2,5-piperazinedione.

1854 (3Z,6Z)-3,6-Dibenzylidene-1-(2-hydroxyethyl)-4-methyl-2,5-piperazinedione.

1856 (3Z,6Z)-3,6-Dibenzylidene-4-methyl-1-phenethyl-2,5-piperazinedione.

1857 (3Z,6Z)-3,6-Dibenzylidene-1-isobutyl-4-methyl-2,5-piperazinedione.

1858 ((3Z,6Z)-3,6-Dibenzylidene-4-methyl-2,5-dioxo-1-piperazinyl)acetonitrile.

1860 (3Z,6Z)-3,6-Dibenzylidene-1-(4-bromoprop-2-enyl)-4-methyl-2,5-piperazinedione.

1862 (3Z,6Z)-3,6-Dibenzylidene-1-(but-2-enyl)-4-methyl-2,5-piperazinedione.

1878 (3Z,6Z)-1-Benzyl-6-(2,6-dichlorobenzylidene)-3-(4-methoxybenzylidene)-4-methyl-2,5-piperazinedione.

1879 (3Z,6Z)-1-Benzyl-6-(4-methoxybenzylidene)-4-methyl-3-(2-nitrobenzylidene)-2,5-piperazinedione.

Compounds of formula A may be prepared by a process which comprises treating a compound of formula B:

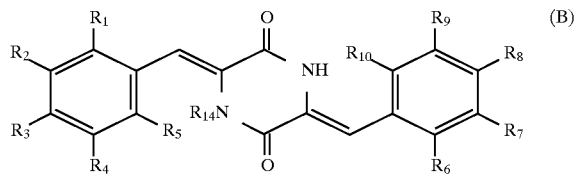

with an alkylating agent, typically an alkyl halide, a dialkyl sulphate, or a sulphonate ester, for example a methanesulphonate or p-toluenesulphonate ester in the presence of a base; to give formula A in which $R^{15}$ or $R^{16}$ is an unsubstituted $C_1$–$C_6$ alkyl group, and/or, if required, removing optionally present protecting groups, and/or, if desired, converting one compound of formula A into another compound of formula A, and/or, if desired, converting a compound of formula A into a pharmaceutically acceptable salt or ester thereof, and/or, if desired, converting a salt or ester into a free compound, and/or, if desired, separating a mixture of isomers into the single isomers.

This alkylation can give rise to a mixture of O-alkylated and N-alkylated products, i.e. a mixture of compounds of formula (Aa) and (Ab), as defined above, wherein $R_{15}$ and $R_{16}$ are the same. The relative proportions of the two products will vary depending on the nature of $R_{15}$ and $R_{16}$, which determines in turn the relative extent of N-alkylation compared to O-alkylation. The two may be separated by conventional methods, for example column chromatography, and obtained separately.

The compound of formula Aa may be prepared by condensing compound of formula (I)

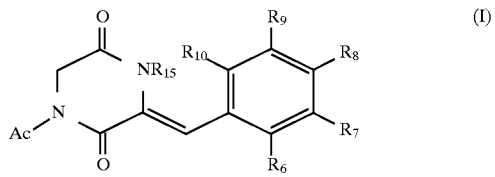

wherein $R_6$ to $R_{10}$ and $R_{15}$ are as defined above and are optionally protected, with a compound of formula (II):

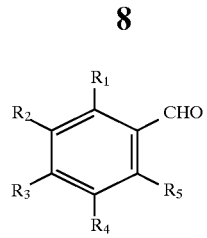

wherein $R_1$ to $R_5$ are defined above and are optionally protected, in the presence of a base in an organic solvent, thereby obtaining a compound of formula A in which $R_{14}$ is hydrogen; or (ii) condensing a compound of formula (I'):

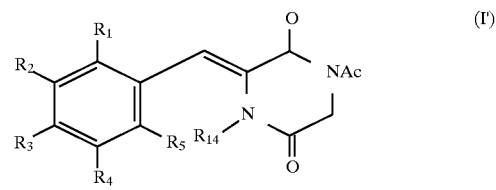

wherein $R_1$ to $R_5$ and $R_{14}$ are as defined above and are optionally protected, with a compound of formula (III):

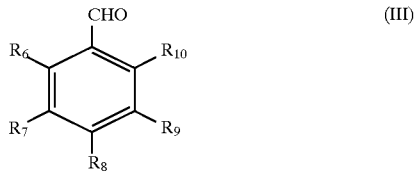

wherein $R_6$ to $R_{10}$ are as defined above and are optionally protected, in the presence of a base in an organic solvent, thereby obtaining a compound of formula A in which $R_{15}$ is hydrogen; and, in either case (i) or (ii), if desired, converting the resulting compound of formula Aa in which $R_{14}$ or $R_{15}$, respectively, is hydrogen into a corresponding compound of formula A in which $R_{14}$, $R_{15}$ or $R_{16}$, respectively, is a $C_1$–$C_6$ alkyl group, by treatment with an alkylating agent; and/or if required, removing optionally present protecting groups and/or, if desired, converting one compound of formula A into another compound of formula A, and/or, if desired, converting a compound of formula A into a pharmaceutically acceptable salt or ester thereof, and/or, if desired, converting a salt or ester into a free compound, and/or, if desired, separating a mixture of isomers of compounds of formula A into the single isomers.

A compound of formula A produced directly by the condensation reaction between (I) and (II) or (I') and (III) may be modified, if desired, by converting one or more of groups $R_1$ to $R_{10}$, into different groups $R_1$ to $R_{10}$. These optional conversions may be carried out by methods known in themselves. For example, a compound of formula A in which one or more of $R_1$ to $R_{10}$ is an ester group may be converted to a compound of formula A wherein the corresponding substituent is a free —COOH group, by acid or alkaline hydrolysis at a suitable temperature, for example from ambient temperature to 1000° C.

A compound of formula A in which one or more of $R_1$ to $R_{10}$ is a —$CO_2H$ group may be converted into a compound of formula A wherein the corresponding substituent is esterified by esterification, for example by treating the carboxylic acid with a suitable $C_1$–$C_6$ alkyl alcohol in the presence of 1,3-dicyclohexylcarbodiimide in an inert solvent.

A compound of formula A in which one or more of $R_1$ to $R_{10}$ is a free —$CO_2H$ group may be converted into a compound of formula A in which the corresponding substituent is a group —$CON(R^{11}R^2)$, wherein $R^{11}$ and $R^{12}$ are as defined above, for example by treatment with ammonia or an amine in the presence of 1,3-dicyclohexylcarbodiimide in an inert solvent.

A compound of formula A in which one or more of $R_1$ to $R_{10}$ is a free —$CO_2H$ group may be converted into a compound of formula A wherein the corresponding substituent is a —$CH_2OH$ group by reduction, for example using borane in a suitable solvent such as tetrahydrofuran.

A compound of formula A in which one or more of $R_1$ to $R_{10}$ is a nitro group may be converted into a compound of formula A in which the corresponding substituent is an amino group by reduction under standard conditions, for example by catalytic hydrogenation.

Protecting groups for $R_1$ to $R_{10}$ in any of the compounds of formulae (I), (I'), (II) and (III) are optionally introduced prior to step (i) or step (ii) when any of groups $R_1$ to $R_{10}$ are groups which are sensitive to the condensation reaction conditions or incompatible with the condensation reaction, for example a —COOH, —$CH_2OH$ or amino group. The protecting groups are then removed at the end of the process. Any conventional protecting group suitable for the group $R_1$ to $R_{10}$ in question may be employed, and may be introduced and subsequently removed by well-known standard methods.

The condensation reaction between compounds (I) and (II) or (I') and (III) is suitably performed in the presence of a base which is potassium t-butoxide, sodium hydride, potassium carbonate, sodium carbonate, caesium carbonate, sodium acetate, potassium fluoride on alumina, or triethylamine in a solvent such as dimethylformamide, or in the presence of potassium t-butoxide in t-butanol or a mixture of t-butanol and dimethylformamide. The reaction is typically performed at a temperature from 0° C. to the reflux temperature of the solvent.

The alkylation of a compound of formula A wherein $R_{14}$ or $R_{15}$ is H is carried out using an appropriate conventional alkylating agent such as a haloalkane, for example an iodoalkane, or a dialkylsulphate, in the presence of a base in an organic solvent. The base may be, for example, sodium hydride, sodium carbonate or potassium carbonate. A suitable base is then DMF. Another suitable base is aqueous sodium hydroxide, in which case a suitable cosolvent is, for example, dioxan, THF or DMF.

The compounds of formula (I) may be prepared by a process comprising reacting 1,4-diacetyl-2,5-piperazinedione with a compound of formula (III) as defined above, in the presence of a base in an organic solvent, thereby obtaining a compound of formula (I) wherein $R_{15}$ is hydrogen; and, if desired, treating the resulting compound of formula (I) with an alkylating agent to obtain a compound of formula (I) in which $R_{15}$ is a $C_1$–$C_6$ alkyl group. Similarly, the compounds of formula (I') may be prepared by a process which comprises reacting 1,4-diacetyl-2,5-piperazinedione with a compound of formula (II) as defined above, in the presence of a base in an organic solvent, thereby obtaining a compound of formula (I') in which $R_{14}$ is hydrogen; and, if desired, treating the resulting compound of formula (I') with an alkylating agent to obtain a compound of formula (I') in which $R_{14}$ is a $C_1$–$C_6$ alkyl group.

If necessary, the resulting compound of formula (I) or (I') can be separated from other reaction products by chromatography.

The reaction of 1,4-diacetyl-2,5-piperazinedione with the compound of formula (III) or (II) is suitably performed under the same conditions as described above for the condensation between compounds (I) and (II), or (I') and (III).

The alkylation of a compound of formula (I) in which $R_{15}$ is hydrogen, or a compound of formula (I') in which $R_{14}$ is hydrogen, is suitably carried out using the same conventional alkylating agents and under the same conditions as described above for the alkylation of compounds of formula (A) in which $R_{14}$ is hydrogen. The alkylation step in the case of a compound (I) where $R_{15}$ is hydrogen typically gives rise to a mixture of the compound of formula (I) in which $R_{15}$ is a $C_1$–$C_6$ alkyl group and its isomer of the following formula (IV) in which $R_1$ is a $C_1$–$C_6$ alkyl group:

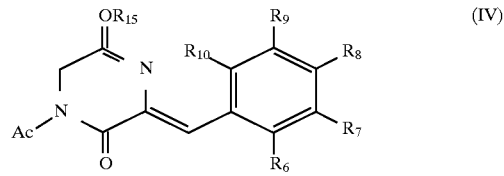

The alkylation step in the case of a compound (I') where $R_{14}$ is hydrogen typically gives rise to a mixture of the compound of formula (I') where $R_{14}$ is a $C_1$–$C_6$ alkyl group and its isomer of formula (IV') where $R_{14}$ is a $C_1$–$C_6$ alkyl group:

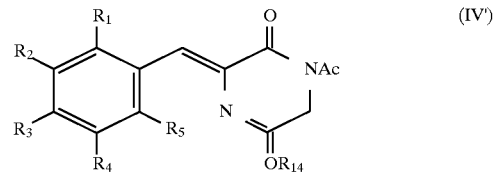

The mixture of compounds (I) and (IV), where $R_{15}$ is other than hydrogen, or compounds (I') and (IV'), where $R_{14}$ is other than hydrogen, can readily be separated by chromatography, for example on silica gel. Suitable eluants include ethyl acetate and hexane, or methanol and dichloromethane.

The substituted benzaldehydes of formulae (II) and (III) are known compounds or can be prepared from readily available starting materials by conventional methods. The 1,4-diacetyl-2,5-piperazinedione used as a starting material in the preparation of compounds of formula (I) may be prepared by treating 2,5-piperazinedione (glycine anhydride) with an acetylating agent. The acetylation may be performed using any conventional acetylating agent, for example acetic anhydride under reflux or, alternatively, acetic anhydride at a temperature below reflux in the presence of 4-dimethylaminopyridine.

Compounds of formula (I) wherein $R_{15}$ is H may also be prepared by the microwave irradiation of a mixture comprising 1,4-diacetyl-2,5-piperazinedione, a compound of formula (III) and potassium fluoride on alumina (as base) in the absence of solvent.

Compounds of formula (I) wherein $R_{15}$ is H may alternatively be prepared directly from 2,5-piperazinedione (glycine anhydride) by a process which comprises treating the 2,5-piperazinedione with a mixture comprising a compound of formula (III), sodium acetate and acetic anhydride at an elevated temperature, for example under reflux.

Compounds of formula (I') wherein $R_{14}$ is H may be prepared by analogous processes, replacing compound (III) in each case by a compound of formula (II).

Compounds of formula A may also be prepared by a process comprising the microwave irradiation of (i) a mixture comprising a compound of formula (I) as defined above wherein $R_{15}$ is H or $C_1$–$C_6$ alkyl, a compound of formula (II) and potassium fluoride on alumina, or (ii) a mixture comprising a compound of formula (I') wherein $R_{14}$ is H or $C_1$–$C_6$ alkyl a compound of formula (III) and potassium fluoride on alumina, or (iii) a mixture comprising 1,4-diacetylpiperazine-2,5-dione, a compound of formula (II), a compound of formula (III) and potassium fluoride on alumina. The irradiation is performed in the absence of a solvent. The resulting compound in which $R_{14}$ and $R_{15}$ are both H may then be alkylated using an appropriate alkylating agent, for example as described above.

Compounds of formula A may also be obtained directly by a process which comprises condensing together 1,4-diacetyl-2,5-piperazinedione, a compound of formula (II) and a compound of formula (III) in the presence of a base in an organic solvent. Suitable bases, solvents and reaction conditions are as described above for the condensation reaction between, for example, compounds (I) and (II).

An alternative direct process for the preparation of compounds of formula A comprises condensing together 2,5-piperazinedione, a compound of formula (II) and a compound of formula (III) in the presence of sodium acetate and acetic anhydride at elevated temperature, for example under reflux.

An alternative process for the preparation of compounds of formula (I) comprises treating a compound of formula (V):

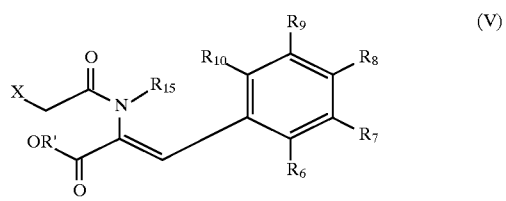

wherein $R_6$ to $R_{10}$ are as defined above, X is a halogen and R' is a $C_1$–$C_6$ alkyl group, with ammonia followed by acetic anhydride.

Compounds of formula (I') may be prepared by an analogous process which comprises treating a compound of formula (V'):

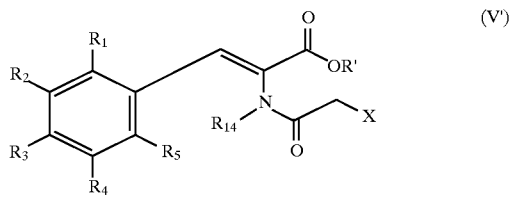

wherein $R_1$ to $R_5$, X and $R^1$ are as defined above, with ammonia followed by acetic anhydride.

X in formula (V) or (V') is typically iodine. R' is, for example, a $C_1$–$C_4$ alkyl group such as a methyl, ethyl, propyl, i-propyl, butyl, sec-butyl or tert-butyl group.

A review of synthetic approaches to unsaturated 3-monosubstituted and 3,6-disubstituted-2,5-piperazinediones is provided in *Heterocycles,* 1983, 20, 1407 (C.Shin).

Compounds of formula (A) may be converted into pharmaceutically acceptable salts, and salts may be converted into the free compound, by conventional methods. Suitable salts include salts with pharmaceutically acceptable inorganic or organic bases, or pharmaceutically acceptable inorganic or organic acids. Examples of inorganic bases include ammonia and carbonates, hydroxides and hydrogen carbonates of group I and group II metals such as sodium, potassium, magnesium and calcium. Examples of organic bases include aliphatic and aromatic amines such as methylamine, triethylamine, benzylamine, dibenzylamine or α-or β-phenylethylamine, and heterocyclic bases such as piperidine, 1-methylpiperidine and morpholine. Examples of inorganic acids include hydrochloric acid, sulphuric acid and orthophosphoric acid. Examples of organic acids include p-toluenesulphonic acid, methanesulphonic acid, mucic acid and succinic acid.

Compounds of formula (A) may also be converted into pharmaceutically acceptable esters. Suitable esters include branched or unbranched, saturated or unsaturated $C_1$–$C_6$ alkyl esters, for example methyl, ethyl and vinyl esters.

Cancer cells which exhibit multiple drug resistance, referred to as MDR cells, display a reduction in intracellular drug accumulation compared with the corresponding drug-sensitive cells. Studies using in vitro derived MDR cell lines have shown that MDR is often associated with increased expression of a plasma membrane glycoprotein (P-gp) which has drug binding properties. P-gp is thought to function as an efflux pump for many hydrophobic compounds, and transfection studies using cloned P-gp have shown that its overexpression can confer the MDR phenotype on cells: see, for example, Ann. Rev. Biochem 58 137–171 (1989).

A major function of P-gp in normal tissues is to export intracellular toxins from the cell. There is evidence to suggest that overexpression of P-gp may play a clinical role in multiple drug resistance. Increased levels of P-gp mRNA or protein have been detected in many forms of human cancers—leukaemias, lymphomas, sarcomas and carcinomas. Indeed, in some cases P-gp levels have been found to increase in tumour biopsies obtained after relapse from chemotherapy.

Inhibition of P-gp function in P-gp mediated MDR has been shown to lead to a net accumulation of anti-cancer agent in the cells. For example, Verapamil a known calcium channel blocker was shown to sensitise MDR cells to Vinca alkaloids in vitro and in vivo: *Cancer Res.,* 41, 1967–1972 (1981). The proposed mechanism of action involves competition with the anti-cancer agent for binding to the P-gp. A range of structurally unrelated resistance-modifying agents acting by this mechanism have been described such as tamoxifen (Nolvadex:ICI) and related compounds, and cyclosporin A and derivatives.

Compounds of formula A and their pharmaceutically acceptable salts and esters (hereinafter referred to as "the present compounds") have been found in biological tests to have activity in modulating multiple drug resistance. The results are set out in Example 3 which follows. The present compounds may therefore be used as multiple drug resistance modifying agents, also termed resistance-modifying agents, or RMAs. The present compounds can modulate, e.g. reduce, or eliminate multiple drug resistance. The present compounds can therefore be used in a method of potentiating the cytotoxicity of an agent which is cytotoxic to a tumour cell. Such a method comprises, for instance, administering one of the present compounds to the tumour cell whilst the tumour cell is exposed to the cytotoxic agent in question. The therapeutic effect of a chemotherapeutic, or antineoplastic, agent may thus be enhanced. The multiple drug resistance of a tumour cell to a cytotoxic agent during chemotherapy may be reduced or eliminated.

The present compounds can also be used in a method of treating a disease in which the pathogen concerned exhibits multi-drug resistance, for instance multi-drug resistant forms of malaria (*Plasmodium falciparum*), tuberculosis, leishmaniasis and amoebic dysentery. Such a method comprises, for instance, administering one of the present compounds with (separately, simultaneously or sequentially) the drug to which the pathogen concerned exhibits multi-drug resistance. The therapeutic effect of the drug may thus be enhanced.

A human or animal patient harbouring a tumour may be treated for resistance to a chemotherapeutic agent by a method comprising the administration thereto of one of the present compounds. The present compound is administered in an amount effective to potentiate the cytotoxicity of the said chemotherapeutic agent. Examples of chemotherapeutic or antineoplastic agents which are preferred in the context of the present invention include Vinca alkaloids such as vincristine and vinblastine; anthracycline antibiotics such as daunorubicin and doxorubicin; mitoxantrone; actinomycin D and plicamycin.

In addition, a human or animal patient suffering from a disease in which the responsible pathogen exhibits multi-drug resistance may be treated for resistance to a therapeutic agent by a method comprising the administration thereto of one of the present compounds.

Examples of such disease include multi-drug resistant forms of malaria (*Plasmodium falciparum*), tuberculosis, leishmaniasis and amoebic dysentery.

MDR modulators also have utility in the delivery of drugs across the blood-brain barrier, and in the treatment of AIDS and AIDS-related complex. The present compounds can therefore be used in a method of facilitating the delivery of drugs across the blood brain barrier, and in the treatment of AIDS or AIDS-related complex. A human or animal patient in need of such treatment may be treated by a method comprising the administration thereto of one of the present compounds.

The present compounds can be administered in a variety of dosage forms, for example orally such as in the form of tablets, capsules, sugar- or film-coated tablets, liquid solutions or suspensions or parenterally, for example intramuscularly, intravenously or subcutaneously. The present compounds may therefore be given by injection or infusion.

The dosage depends on a variety of factors including the age, weight and condition of the patient and the route of administration. Typically, however, the dosage adopted for each route of administration when a compound of the invention is administered alone to adult humans is 0.001 to 10 mg/kg, most commonly in the range of 0.01 to 5 mg/kg, body weight. Such a dosage may be given, for example, from 1 to 5 times daily by bolus infusion, infusion over several hours and/or repeated administration.

A piperazine of formula (A) or a pharmaceutically acceptable salt or ester thereof is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. An agent for use as a modulator of multiple drug resistance comprising any one of the present compounds is therefore provided.

For example, the solid oral forms may contain, together with the active compound, diluents such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methylcellulose, carboxymethylcellulose, or polyvinyl pyrrolidone; disintegrating agents such as starch, alginic acid, alginates or sodium starch glycolate; effervescing mixtures; dyestuffs; sweeteners; wetting agents such as lecithin, polysorbates, lauryl sulphates. Such preparations may be manufactured in known manners, for example by means of mixing, granulating, tabletting, sugar coating, or film-coating processes.

Liquid dispersions for oral administration may be syrups, emulsions and suspensions. The syrups may contain as carrier, for example, saccharose or saccharose with glycerol and/or mannitol and/or sorbitol. In particular, a syrup for diabetic patients can contain as carriers only products, for example sorbitol, which do not metabolise to glucose or which only metabolise a very small amount to glucose. The suspensions and the emulsions may contain as carrier, for example, a natural gum, agar, sodium alginate, pectin, methylcellulose, carboxymethylcellulose or polyvinyl alcohol.

Suspensions or solutions for intramuscular injections may contain, together with the active compound, a pharmaceutically acceptable carrier such as sterile water, olive oil, ethyl oleate, glycols such as propylene glycol, and, if desired, a suitable amount of lidocaine hydrochloride. Some of the present compounds are insoluble in water. Such compounds may be encapsulated within liposomes.

The following Examples illustrate the invention:

REFERENCE EXAMPLE 1

Preparation of (3Z,6Z)-6-Benzylidene-3-(4-methoxybenzylidene)-2,5-piperazinedione (3)
(scheme 1)

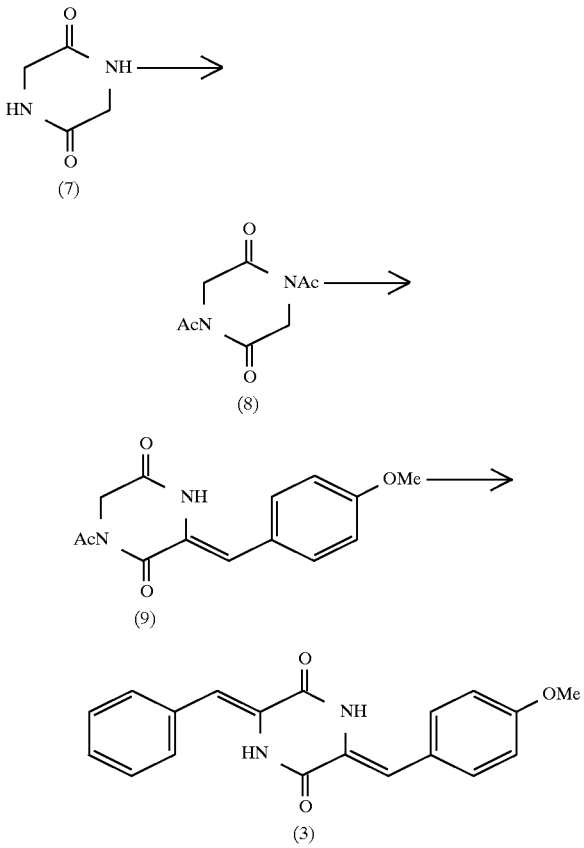

1,4-Diacetyl-2,5-piperazinedione (8)

1,4-Diacetyl-2,5-piperazinedione (8) was prepared by the published procedure (S. M. Marcuccio and J. A. Elix, *Aust. J. Chem.*, 1984, 37, 1791).

(3Z)-1-Acetyl-3-(4-methoxybenzylidene)-2,5-piperazinedione (9)

(3Z)-1-Acetyl-3-(4-methoxybenzylidene)-2,5-piperazinedione (9) was prepared by the published procedure (T. Yokoi, L.-M. Yang, T. Yokoi, R.-Y. Wu, and K.-H. Lee, *J. Antibiot.*, 1988, 41, 494).

(3Z,6Z)-6-Benzylidene-3-(4-methoxybenzylidene)-2,5-piperazinedione (3)

A mixture of (3Z)-1-acetyl-3-(4-methoxybenzylidene)-2,5-piperazinedione (9) (1.0 g, 3.6 mmol), benzaldehyde (430 μl, 4.2 mmol) and triethylamine (1.14 ml), 8.2 mmol), in dry DMF (20 ml), was heated at 130° C. for 18 h. The reaction mixture was cooled to room temperature and poured into ethyl acetate (100 ml). A yellow solid precipitated which was filtered off and dried. Yield 360 mg (31%).

$^1$H nmr (400 MHz $d_6$-DMSO): δ: 3.80 (3H, s, O—Me); 6.77 (1H, s, CH=C); 6.78 (1H, s, CH=C); 6.98 (2H, d, J=8 Hz, 2×C—H on Ar—OMe) ; 7.30–7.56 (7H, m, Ph and 2×C—H on Ar—OMe); 10.15 (2H, br.s, N—H).

$^{13}$C nmr (100 MHz $d_6$-DMSO) δ: 58.68; 117.66; 118.03; 118.77; 128.11; 128.92; 129.95; 131.53; 132.11; 132.69; 134.44; 136.59; 161.39; 161.62; 162.71.

ms (desorption chemical ionisation, ammonia):

m/z (% relative intensity) : 321 (100) MH$^+$.

ir: KBr (diffuse reflectance):

ν max (cm$^{-1}$) : 1620, 1700, 3100, 3220.

Elemental analysis: Calculated for $C_{19}H_{16}N_2O_3$: C 71.24, H 5.03, N 8.74. Found: C 70.92, H 5.02, N 8.80. C 70.89, H 5.06, N 8.79

REFERENCE EXAMPLE 2

Preparation of (3Z,6Z)-6-Benzylidene -3-(4-methoxybenzylidene)-2,5-piperazinedione (3) (scheme 2)

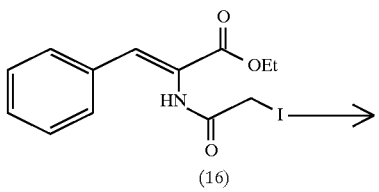

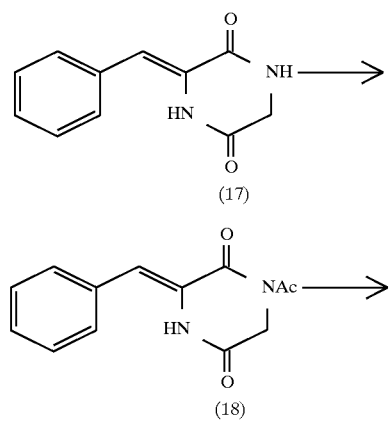

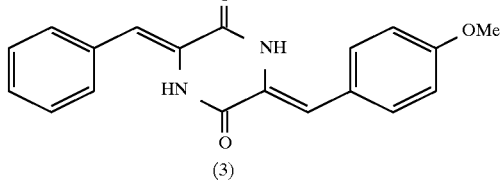

Compound 16 is treated with ammonia and subsequently with acetic anhydride to yield 1-acetyl-3-benzylidene-2,5-piperazinedione (18).

Compound 18 is then condensed, in the presence of caesium carbonate or triethylamine in DMF, with 4-methoxybenzaldehyde to yield compound 3.

REFERENCE EXAMPLE 3

Preparation of 1-acetyl-3-benzylidene-2,5-piperazinedione 1,4-Diacetyl-2,5-piperazinedione (25.0 g, 126 mmol), which is compound (8) mentioned in Reference Example 1, was heated at 120°–130° C. in DMF (200 ml) with triethylamine (17.6 ml, 126 mmol) and benzaldehyde (13.0 ml, 126 mmol). After 4 h the mixture was cooled to room temperature and poured into EtOAc (1000 ml), and washed three times with brine. Any solid formed at this stage was filtered off. The filtrate was dried (MgSO$_4$) and the solvent removed in vacuo. The residue was recrystallised from EtOAc:Hexane to give 11.78 g (38%) of the title compound as a yellow solid.

$^1$H NMR (CDCl$_3$ 400 MHz) δ=2.69 (3H, s) 4.54 (2H, s) 7.20 (1H, s) 7.40 (3H, m), 7.48 (2H, m), 7.93 (1H, br.s)

MS(DCI,NH$_3$) : 262 (MNH$_4^+$, 20%), 245 (MH$^+$, 53%), 220 (52%), 204 (100%), 203 (100%)

| Microanalysis | C | H | N |
|---|---|---|---|
| Calc | 63.93 | 4.95 | 11.47 |
| Found | 64.11 | 5.02 | 11.41 |
|  | 64.05 | 4.90 | 11.44 |

REFERENCE EXAMPLE 4

Preparation of 1-acetyl-3-(4-acetamidobenzylidene)-2,5-piperazinedione 1,4-Diacetyl-2,5-piperazinedione (10.0 g, 50 mmol), prepared by the published procedure mentioned in Reference Example 1, was stirred in DMF (40 ml) with 4-acetamidobenzaldehyde (8.24 g, 50 mmol) and triethylamine (7 ml, 50 mmol) and heated to 120° C. After 2½ h the mixture was cooled to room temperature, diluted with EtOAc (100 ml) and stirred overnight. The solid formed was collected, washed with EtOAc and dried to give 8.46 g (56%) of a yellow solid.

$^1$H NMR (CDCl$_3$+CF$_3$CO$_2$H, 400 MHz) δ=2.32 (3H, s) 2.72 (3H, s) 4.68 (2H, s) 7.36 (1H, s) 7.45 (2H, d, J=8 Hz) 7.60 (2H, d, J=8 Hz)

| Microanalysis | C | H | N |
|---|---|---|---|
| Calc | 59.80 | 5.02 | 13.95 |
| Found | 60.08 | 5.09 | 13.89 |
|  | 60.11 | 5.07 | 13.86 |

REFERENCE EXAMPLE 5

Preparation of (3Z,6Z)-3-benzylidene -6-(4-methoxybenzylidene)-1-methyl-2,5-piperazine dione (1) (Scheme 4)

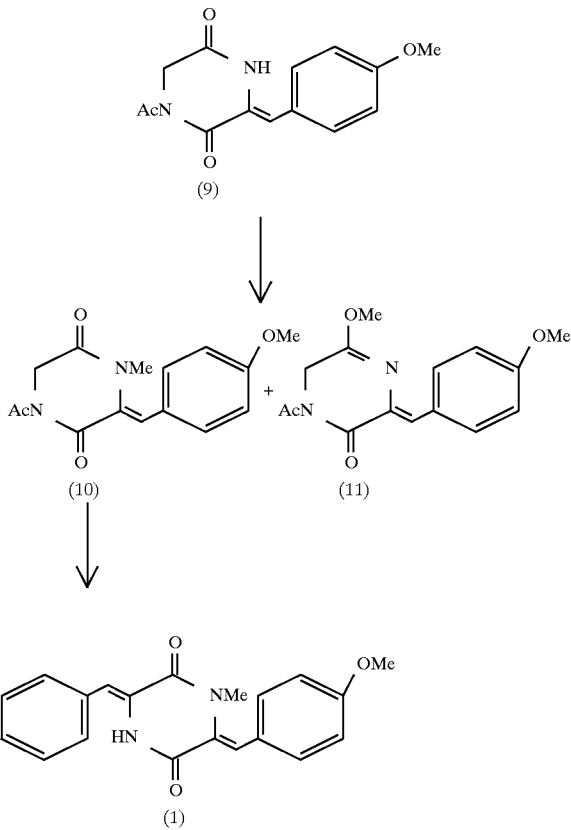

(3Z)-1-Acetyl-3-(4-methoxybenzylidene)-4-methyl-2,5-piperazinedione (10) and 1-Acetyl-5-methoxy-3-(4-methoxybenzylidene)-3,6-dihydropyrazin-2-one (11)

A mixture of (3Z)-1-Acetyl-3-(4-methoxybenzylidene)-2,5-piperazinedione (9) (2.0 g, 7.3 mmol), methyl iodide (0.46 ml, 7.3 mmol), and sodium carbonate (800 mg, 7.5 mmol) in dry DMF (50 ml) was stirred under an atmosphere of dry nitrogen for 3 days. The reaction mixture was then poured into ethyl acetate (500 ml) and washed with water (4×100 ml) and brine. The organic phase was separated, dried (MgSO$_4$), and the solvent removed in vacuo. The residue was purified by flash chromatography (silica, EtOAc:Hexane, 1:1) to give (3Z)-1-acetyl-3-(4-methoxybenzylidene)-4-methyl-2,5-piperazinedione (10) 1.38 g (66%) as a yellow solid and 1-acetyl-5-methoxy-3-(4-methoxybenzylidene)-3,6-dihydropyrazin-2-one (11) 248 mg (11.8%) as a bright yellow solid.

(3Z)-1-Acetyl-3-(4-methoxybenzylidene)-4-methyl-2,5-piperazinedione (10):

$C_{15}H_{16}N_2O_4$ $^1$H nmr (400 MHz CDCl$_3$): δ: 2.63 (3H, s, Ac); 2.95 (3H, s, N—Me); 3.87 (3H, s, O—Me); 4.52 (s, 2H, N—CH$_2$—CO); 6.93 (2H, d, J=8 Hz, Aromatic); 7.26 (1H, s, C=CH); 7.29 (2H, d, J=8 Hz), Aromatic).

ms (desorption chemical ionisation, ammonia):

m/z (% relative intensity): 306 (34%) MNH$_4^+$; 289 (100%); 216 (14%)

ir : KBr (diffuse reflectance) v$_{max}$ (cm$^{-1}$): 1690, 1700, 3000.

Elemental analysis: Calculated for $C_{15}H_{16}N_2O_4$: C 62.49, H 5.59, N 9.72 C 62.48, H 5.58, N 9.68. C 62.51, H 5.65, N 9.67%

1-Acetyl-5-methoxy-3-(4-methoxybenzylidene)-3,6-dihydropyrazin-2-one (11)

$C_{15}H_{16}N_2O_4$ $^1$H nmr (400 MHz CDCl$_3$): δ: 2.68 (3H, s, Ac); 3.86 (3H, s, Ar—OMe); 3.99 (3H, s, O—Me); 4.44 (s, 2H, N—CH$_2$—CO); 6.95 (2H, d, J=8 Hz, Ar); 7.32 (1H, s, C=CH); 8.03 (2H, d, J=8 Hz, Ar).

ms (desorption chemical ionisation, ammonia):

m/z (% relative intensity): 289 (100%) MH$^+$; 247 (14%)

ir : KBr (diffuse reflectance):

v$_{max}$ (cm$^{-1}$): 1610, 1690, 1700, 1740, 2950.

Elemental Analysis: Calculated for $C_{15}H_{16}N_2O_4$: C 62.49, H 5.59, N 9.72. C 62.52, H 5.59, N 9.64. C 62.52, H 5.64, N 9.66%

(3Z, 6Z)-3-Benzylidene-6-(4-methoxybenzylidene)-1-methyl-2,5-piperazinedione (1)

A mixture of (3Z)-1-Acetyl-3-(4-methoxybenzylidene)-4-methyl-2,5-piperazinedione (10) (200 mg, 0.69 mmol) and sodium hydride (60% dispersion in oil, 28 mg, 0.69 mmol) in dry DMF (10 ml) was stirred at room temperature for 18 h. Benzaldehyde (71 μl, 0.69 mmol) was then added and the reaction mixture stirred at room temperature for 18 h. It was then diluted with ethyl acetate (100 ml) and washed with brine (4×50 ml) . The organic phase was separated, dried (MgSO$_4$), and the solvent removed in vacuo. The residue was purified by flash chromatography (silica, dichloromethane containing 1% MeOH) to give 48 mg (21%) of a yellow solid.

$C_{20}H_{18}N_2O_3$ $^1$H nmr (400 MHz CDCl$_3$): δ: 3.06 (3H, s, N—Me); 3.87 (3H, s, O—Me); 6.93 (2H, d, J=8 Hz, 2×C—H on Ar—OMe); 7.06 (1H, s, Ph—CH=C); 7.23 (2H, d, J=8 Hz, 2×C—H on Ar—OMe); 7.27 (1H, s, MeOAr—C$\underline{H}$=C); 7.30–7.48 (5H, m, Ph); (1H, br.s, N—H).

$^{13}$C nmr (100 MHz CDCl$_3$) δ: 36.62; 55.34; 113.86; 116.80; 121.30; 126.02; 126.14; 128.47; 128.78; 129.06; 129.45; 131.11; 133.07; 159.66; 159.68; 159.95.

ms (desorption chemical ionisation, ammonia): 335 (100%) MH$^+$.

ir: KBr (diffuse reflectance): v$_{max}$ (cm$^{-1}$): 1690, 3000, 3180, 3400.

Elemental analysis: Calculated for $C_{20}H_{18}H_2O_3$: O 71.84, H 5.43, N 8.38. C 71.81, H 5.31, N 8.31. C 71.80, H 5.25, N 8.31%.

REFERENCE EXAMPLE 6

Preparation of (3Z,6Z)-3-benzylidene-6-(4-methoxybenzylidene)-1,4-dimethyl-2,5-piperazinedione (2) (Scheme 5)

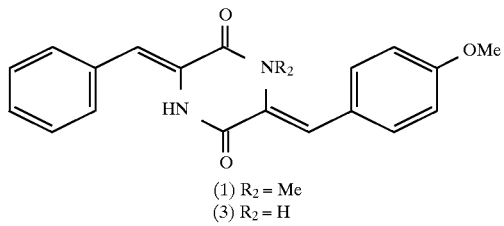

(1) $R_2$ = Me
(3) $R_2$ = H

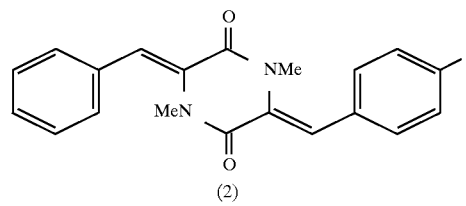

(2)

(3Z,6Z)-3-Benzylidene-6-(4-methoxybenzylidene)-1,4-dimethyl-2,5-piperazinedione (2)

A mixture of (3Z,6Z)-3-Benzylidene-6-(4-methoxybenzylidene)-2,5-piperazinedione (3) (0.5 g, 1.56 mmol), sodium hydride (60% dispersion in mineral oil, 125 mg, 3.1 mmol) and methyl iodide (243 μl, 3.9 mmol) in dry DMF (50 ml) was stirred at room temperature for 4 days. The solvent was then removed in vacuo and the residue purified by flash chromatography (silica, eluting with EtOAc:Hexane, 1:3) to give 220 mg (40%) of compound 2 as a yellow solid.

$C_{21}H_{20}N_2O_3$ $^1H$ nmr (400 MHz $CDCl_3$) δ: 2.95 (3H, s, N—Me); 3.04 (3H, s, N—Me); 3.85 (3H, s, O—Me); 6.90 (2H, d, J=8 Hz, 2×C—H on Ar—OMe); 7.19 (1H, s, CH=C); 7.21 (1H, s, CH=C) 7.30–7.56 (7H, m, Ph and 2×C—H on Ar—OMe).

ms (desorption chemical ionisation, ammonia):

m/z (% relative intensity): 349 (100) $MH^+$.

REFERENCE EXAMPLE 7

Preparation Of Starting Compounds 121 and 122

1-Acetyl-3-benzylidene-2,5-piperazinedione (compound 18 prepared in Reference Example 2) was N-methylated by treatment with methyl iodide (2.0 equivalents) in the presence of $Na_2CO_3$ (1.0 equivalents) in DMF at room temperature for 24 hours. The solvent was removed and the residue purified by flash chromatography. The product 1-acetyl-3-benzylidene-4-methyl-2,5-piperazinedione, obtained in 45% yield, was treated with 4-methoxybenzaldehyde (1.0–1.1 equivalents) in the presence of $Cs_2CO_3$ in DMF at 80° C. for 206 hours to give compound 121, which is (3Z,6Z)-6-benzylidene-3-(4-methoxybenzylidene)-1-methyl-2,5-piperazinedione, in 35% yield.

By an analogous method, but using benzaldehyde in place of 4-methoxybenzaldehyde, compound 122 which is (3Z, 6Z)-3,6-dibenzylidene-1-methyl-2,5-piperazinedione was obtained in 68% yield.

EXAMPLE 1

Compounds of general formula A were prepared using the starting material B and alkylation conditions specified in the following Table 1. Further compounds were synthesised starting appropriately substituted starting compounds B: 1803, 1817, 1818, 1820, 1823, 1824, 1827, 1859 and 1863.

TABLE 1

| Target Compound | Starting Compound B | Alkylation Conditions | Yield |
|---|---|---|---|
| 1780 | Compound 122 (Ref. Ex. 7) | NaH (1.1 eq) cyclohexylmethylbromide DMF, room temperature, 8–10 hours; Flash chromatography | 16% |
| 1801 | Compound 122 | NaH (1 eq) EtI (1 eq) DMF, room temp 8–10 hours; Flash chromatography | 39% |
| 1819 | Compound 122 | As for 1780, but alkylating agent is 2-iodopropane | 12% |
| 1821 | Compound 122 | As for 1780, but alkylating agent is isobutyl iodide. | 27% |
| 1857 | | Products separated by flash chromatography | 36% |
| 1826 | Compound 122 | NaH, (1 eq) 4-bromo-1-butene (1 eq) | 14% |
| 1881 | Compound 122 | DMF, room temp, 4 hrs. Products separated by flash chromatography | 23% |
| 1855 | Compound 122 | NaH (1 eq) 1-bromopentane, DMF, room temp, 8–10 hours, then flash chromatography | 2.5% |
| 1861 | Compound 122 | As for 1855, but alkylating agent is crotyl bromide. | 14% |
| 1862 | | Products separated by flash chromatography | 72% |
| 1900 | Compound 122 | NaH, $Cl(CH_2)_3NMe_2.HCl$, DMF, 24 hours 80° C. Column chromatography 1:1 EtOAc/MeOH) | |
| 1901 | Compound 122 | NaH, 4-chloromethyl-pyridine, DMF, 24 hours, room temp. Column chromatography 1:1 EtOAc/hexane | |
| 1902 | Compound 122 | NaH, N-(2-bromoethyl)phthalimide DMF; recyrstallised from hexane | |
| 1903 | Compound 122 | NaH, N-(4-bromobutyl)phthalimide, DMF; column chromatography 1:2 EtOAc/hexane, recrystallised from EtOAC | |
| 1904 | Compound 122 | NaH, 4-bromobutyl acetate DMF; column chromatography 1:3 EtOAc/hexane | |
| 1905 | Compound 122 | NaH, N-(bromomethyl)phthalimide, DMF; recrystallised from EtOAc/hexane | |
| 1932 | Compound 122 | (i) NaH, DMF, 10 mins (ii) N-(3-chloropropyl) succinimide), $Bu_4NI$, 18 hours, 65° C. (iii) Column chromatography, silica, EtOAc:hexane 1:2–2:1 | 7% |
| 1934 | Compound 122 | (i) NaH, DMF, 10 mins (ii) N-(3)-chloropropyl) succinimide, $Bu_4NI$, 70° C., 18 hours (iii) Column (silica, EtOAc, hexane, 1:3–1:1), recrystallised from EtOAc/hexane) | |
| 1935 | Compound 122 | (i) NaH, DMF, 10 mins | 33% |

TABLE 1-continued

| Target Compound | Starting Compound B | Alkylation Conditions | Yield |
|---|---|---|---|
| | | (ii) Bu₄NI, 80° C., 18 hours, N-(3-chloropropyl)isatin (ii) Column: silica, EtOAc: hexane 1:4–1:2 | |
| 1936 | Compound 122 | (i) NaH, DMF, (ii) 0° C., 3-bromomethyl-nitrobenzene, 2 hours (ii) Column (EtOAc/hexane, 1:3) | |
| 1939 | Compound 122 | (i) DMF, NaH (1 eq) (ii) 0° C., 4-bromomethyl-nitrobenzene (1 eq), 2 hours (iii) Column, EtOAc/hexane | |
| 1825 | Compound 122 | NaH (1 eq), DMF, 10 mins, allyl bromide, r.t. overnight | 68% |
| 1864 | | | 29% |

EXAMPLE 2

Pharmaceutical Composition

Tablets, each weighing 0.15 g and containing 25 mg of a compound of the invention can be manufactured as follows:

Composition for 10,000 tablets compound of the invention (250 g)

lactose (800 g)

corn starch (415 g)

talc powder (30 g)

magnesium stearate (5 g)

The compound of the invention, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium stearate is added, carefully mixed and processed into tablets.

EXAMPLE 3

Testing of compounds A as modulators of MDR

Materials and Methods

The EMT6 mouse mammary carcinoma cell line and the MDR resistant subline AR 1.0 were cultured in RPMI 1640 medium containing 10% foetal calf serum and 2 mM glutamine at 37° C. in 5% $CO_2$. Cells were passaged between 1 in 200 and 1 in 2000 in the case of the parental cell line and between 1 in 20 and 1 in 200 in the case of the MDR resistant subline, after trypsinisation (0.25% trypsin, 0.2 gl$^{-1}$, EDTA).

1. Drug accumulation assay

AR 1.0 cells were seeded into 96 well opaque culture plates (Canberra Packard). The assay medium contained a mixture of tritiated Daunorubicin (DNR), a cytotoxic agent, and unlabelled DNR (0.25μ Ci/ml; 2 μM). Compounds of formula A were serially diluted in assay medium over a range of concentrations from 100 nM to 100 μM. The cells were incubated at 37° C. for 1 hr before washing and counting of cell associated radioactivity. Each assay included a titration of the known resistance modifying agent Verapamil as positive control. Results were expressed as % maximum accumulation where 100% accumulation is that observed in the presence of 100 μM Verapamil.

The results are set out in the following Tables 2, 3 and 4.

TABLE 2

| Compound No. | IC50 (μm) Accumulation | MAX accumulation (% 100 μm VRP) |
|---|---|---|
| 1454 | 10.0 | — |
| 1486 | 50.0 | — |
| 1490 | 30.0 | 63.6 |
| 1500 | 15.0 | 91.3 |
| 1521 | 30.0 | 65.2 |
| 1526 | — | 23.3 |
| 1527 | 40.0 | 73.9 |
| 1614 | — | 25.0 |
| 1745 | — | 35.0 |
| 1747 | 10.0 | 100.0 |
| 1771 | 70.0 | 60.0 |
| 1779 | 15.0 | — |
| 1780 | — | 20.0 |
| 1801 | — | 40.0 |
| 1803 | 80.0 | 50.0 |
| 1817 | 20.0 | — |
| 1818 | 7.0 | — |
| 1819 | — | 23.0 |
| 1820 | — | 34.0 |
| 1821 | — | 35.0 |
| 1822 | 9.0 | — |
| 1823 | 9.0 | — |
| 1824 | 3.0 | — |
| 1825 | 10.0 | — |
| 1826 | — | 40.0 |
| 1827 | — | 35.0 |
| 1833 | 12.0 | — |
| 1854 | 35.0 | — |
| 1855 | 10.0 | — |
| 1856 | 15.0 | — |
| 1857 | 10.0 | — |
| 1858 | 60.0 | — |
| 18S9 | 15.0 | — |
| 1860 | 10.0 | — |
| 1861 | — | 46.0 |
| 1862 | 8.0 | — |
| 1863 | 10.0 | — |
| 1864 | — | 45.0 |
| 1878 | 5.0 | — |
| 1879 | 2.0 | — |
| 1900 | 3.0 | — |
| 1901 | 12.0 | — |
| 1902 | 11.0 | — |
| 1903 | 9.0 | — |
| 1904 | — | 47.0 |
| 1905 | — | 29.0 |
| 1906 | — | 34.0 |
| 1936 | 2.0 | — |
| 1939 | 4.0 | — |

TABLE 3

| Compound No. | Conc Comp (μM) | Potentiation Index |
|---|---|---|
| 1454 | 5 | 10 |
| 1500 | 5, 3, 5, 5 | 10, 10, 13, 25 |
| 1747 | 5 | 20 |
| 1779 | 5 | 40 |
| 1823 | 3 | 20 |
| 1824 | 3, 3, 5, 5 | 60, 80, 80, 400 |
| 1825 | 3 | 15 |
| 1833 | 3 | 20 |

TABLE 4

| COMPOUND NO. | CONC CYTOTOXIC AGENT (μg/ml) | COMPOUND TOXICITY (IC50 μM) | TOXICITY WITH CYTOTOXIC AGENT (IC 50 μM) |
|---|---|---|---|
| 1454 | 1.00 | 5.0 | 0.5 |
| 1486 | 1.00 | 10.0 | 1.0 |
| 1490 | 1.00 | 30.0 | 2.0 |
| 1500 | 0.50 | 20.0 | 2.0 |
| 1521 | 1.00 | 70.0 | 30.0 |
| 1527 | 1.00 | 40.0 | 1.5 |
| 1612 | 1.00 | — | 0.0 |
| 1747 | 1.00 | 7.0 | 0.3 |
| 1779 | 1.00 | 15.0 | 0.8 |
| 1817 | 0.50 | 20.0 | 1.5 |
| 1818 | 0.50 | 1.5 | 0.8 |
| 1822 | 0.50 | 5.0 | 0.5 |
| 1823 | 0.50 | 30.0 | 0.7 |
| 1824 | 0.50 | 7.0 | 0.3 |
| 1825 | 0.50 | 20.0 | 1.5 |
| 1833 | 0.50 | 9.0 | 1.0 |
| 1855 | 0.50 | 6.0 | 0.8 |

2. Potentiation of Doxorubicin toxicity

Compounds of formula A were examined for their ability to potentiate the toxicity of doxorubicin in AR 1.0 cells. In initial proliferation assays compounds were titrated against a fixed concentration of doxorubicin (0.5–1 μM) which alone is non-toxic to AR 1.0 cells. Incubations with doxorubicin were over a four day period before quantitation of proliferation using the colorimetric sulphorhodamine B assay (Skehan et al; J. Natl. Cancer Inst. 82 pp 1107–1112 (1990))

Compounds which were shown to be able to sensitise AR 1.0 cells to 0.8–1.7 μM doxorubicin without high innate toxicity were selected for further study. Cells were cultured for four days with concentrations of doxorubicin over the range of 0.5 nM–50 μM in the presence of Verapramil at its maximum subtoxic level determined from previous experiments. Proliferation was quantified as described by Skehan et al, loc cit. The $IC_{50}$ (concentration required to reduce proliferation to 50% of the untreated controls) for doxorubicin alone and with the compound of formula A were derived and used to calculate the potentiation index (PI):

$$PI = \frac{IC_{50} \text{ for Doxorubicin alone}}{IC_{50} \text{ for Doxorubicin plus } RMA}.$$

EXAMPLE 4

Characterization of compounds of formula A

The compounds prepared in Examples 1 to 3 were characterised by conventional mass spectroscopic, microanalytical, proton nmr and i.r. techniques. The results are set out in Table 5.

TABLE 5

| No. | Mol. Formula (M. Wt) | Mass spec m/z, mass intensity (mode) | $^1$H nmr Solvent δ all 400 MHz | Microanalysis Calc | | Found |
|---|---|---|---|---|---|---|
| 1779 | $C_{26}H_{22}N_2O_2$ | 395(M+H)$^+$(100%) (CI,NH$_3$) | CDCl$_3$ 7.48–7.15(15H, m), 6.98–6.40(2H, m), 4.75(2H, 3), 2.95(3H, s) | C 79.17<br>H 5.62<br>N 7.10 | 79.12<br>5.61<br>6.99 | 79.18<br>5.66<br>7.06 |
| 1486 | $C_{22}H_{20}N_2O_5$ = 392 | MH$^•$393,MNH$_4^•$410(10%) DCI,NH$_3$ | CDCl$_3$ δ$_H$:7.98(1H, bs), 7.48(4H, m), 7.38(1H, m), 7.30(1H, s), 7.28(2H, m), 7.05(1H, s), 6.90(2H, d), 4.35(2H, s), 3.87(3H, s) 3.65(3H, s) | C 67.34<br>H 5.14<br>N 7.14 | 67.46<br>5.02<br>7.11 | 67.26<br>5.19<br>7.08 |
| 1879 | | | CDCl$_3$ 400, J$_z$ 3.03(3H, s), 3.86(3H, s), 4.59(2H, s), 6.86(2H, m), 6.93(2H, d), 7.19(3H, m) 7.26–7.31(3H, multiple peaks), 7.36–7.45, (2H, multiple peaks) 7.51(1H, t), 7.58(1H, t), 8.12(1H, d). | | | |
| 1878 | $C_{27}H_{22}N_2O_3Cl_2$ = 493 | 493/495 100%/60% 510/512 14%/9% DCI NH$_3$ | CDCl$_3$ 3.03(3H, s) 3.86(3H, s), 4.57(2H, s), 6.89–6.95(4H, multiple | | | |

TABLE 5-continued

| No. | Mol. Formula (M. Wt) | Mass spec m/z, mass intensity (mode) | ¹H nmr Solvent δ all 400 MHz | Microanalysis Calc | Found |
|---|---|---|---|---|---|
| | | | signals), 7.18–7.35(overlapping sample & solvent). | | |
| 1862 | $C_{23}H_{22}N_2O_2$ | 359(H+H)⁺(100%) CI,NH₃ | CDCl₃ 7.42→7.28(10H, m), 7.24→7.17(2H, m), 5.24→5.11(2H, m), 4.13(2H, d), 2.98(3H, s), 1.57(3H, d). | | |
| 1860 | $C_{23}H_{21}BrN_2O_2$ | 479(H+43)⁺(9%), 439(M+H)⁺(96%), 437(M+H)⁺(91%), 357(100%). CI,C₄H₁₀ | CDCl₃ 7.44→7.29(10H, m), 7.22(2H, s), 5.56→5.47(1H, m) 5.42→5.32(1H, m) 4.22(2H, d), 3.78(2H, d), 2.98(3H, s) | | |
| 1858 | $C_{21}H_{17}N_3O_2$ | 361(M+NH₄)⁺(48%) 343(M+H)⁺(100%) CI,NH₃ | CDCl₃ 7.49→7.32(10H, m), 7.27(2H, d), 4.35(2H, s), 3.01(3H, s). | | |
| 1856 | $C_{27}H_{24}N_2O_2$ | 409(m+H)⁺(100%) CI,NH₃ | CDCl₃ 7.43→7.22(10H, m), 7.22–7.10(5H, m) 6.93(2H, d), 3.86(2H, t), 2.83(3H, s), 2.72(2H, t). | | |
| 1854 | $C_{21}H_{20}N_2O_3$ | 349(H+H)⁺(100%) CI,NH₃ | CDCl₃ 7.44→7.28(10H, m), 7.23(1H, s), 7.18(1H, s), 3.73(2H, t), 3.64→3.58(2H, s, br), 2.99(3H, s), 2.02→1.91(1H, s, br). | | |
| 1825 | $C_{22}H_{20}N_2O_2$ | 345(M+H)⁺(100%) CI,NH₃ | CDCl₃ 7.42→7.28 (10H, m), 7.20(2H, d), 5.63→5.52(1H, m), 5.01(1H, d), 4.77(1H, dd), 4.21(2H, d), 2.98(3H, s). | | |
| 1823 | $C_{24}H_{24}N_2O_4$ | 447(M+C₃H₇)⁺(3%), 405(M+H)⁺(100%) CI,C₄H₁₀ | CDCl₃ 7.46→7.28(10H, m), 7.18(1H, s), 7.14(1H, s), 4.74(1H, t), 3.90→3.80(2H, m), 3.28→3.17(4H, m), 2.98(3H, s), 1.89→1.78(2H, m). | | |
| 1803 | $C_{21}H_{19}N_3O_2Br$ | 428,430(M+NH₄)⁺, 411,413(M+H)⁺ CI,NH₃ | CDCl₃ 7.38→7.22(10H, m), 7.14(2H, s), 3.85(2H, t), 3.33(2H, t), 2.92(3H, s). | C 61.33 H 4.66 N 6.81 Br 19.43 | 61.32 61.28 4.70 4.62 6.72 6.66 19.32 19.06 |
| 1614 | $C_{23}H_{23}N_3O_4$ = 405 | MH• 406 DCI NH₃ | CDCl₃ δ_H:8.02(1H, bs), 7.45(4H, m), 7.40(3H, m), 7.22(1H, s), 7.05(1H, s), 6.95(2H, d), 4.48(2H, s), 4.35(3H, s), 2.88(3H, s), | | |

TABLE 5-continued

| No. | Mol. Formula (M. Wt) | Mass spec m/z, mass intensity (mode) | $^1$H nmr Solvent δ all 400 MHz | Microanalysis | | |
|---|---|---|---|---|---|---|
| | | | | | Calc | Found |
| 1527 | $C_{25}H_{27}N_3O_4$ mw = 433 | 434(m$^+$, 100%) 361(12%) DCI-NH$_3$ | 2.65(3H, s). CDCl$_3$ 0.83(3H, t), 1.05(3H, t), 2.87(2H, δ), 3.25(2H, δ), 3.81(3, H, s), 4.42(2H, s), 6.98(2H, d), 7.00(1H, s), 7.28(1H, s), 7.30–7.42(7H, m), 7.98(1H, bs). | | | |
| 1526 | $C_{25}H_{25}N_3O_4$ mw = 431 | 432(m$^+$H, 100%), 361(15%) DCI-NH$_3$ | CDCl$_3$ 1.69–1.80(4H, m), 2.78(2H, t) 3.33(2H, t), 3.80(3H, s), 4.33(2H, s), 6.96(2H, d), 7.00(1H, s), 7.25(1H, s), 7.27–7.40(4H, m), 8.01(1H, bs). | | | |
| 1521 | $C_{25}H_{25}N_3O_4$ = 431 | MH$^·$432 DCINH$_3$ | CDCl$_3$ δ$_H$:7.98(1H, bs), 7.45(4H, m), 7.34 (3H, m), 7.25(1H, s), 7.05(1H, s), 6.95(2H, d), 4.37(2H, s), 3.85(3H, s), 3.40(2H, t), 3.00(2H, t), 1.85(2H, m), 1.78(2H, m). | C H N | 69.59 5.84 9.74 | 69.43 5.67 9.63 | 69.52 5.67 9.63 |
| 1490 | $C_{22}H_{20}N_2O_5$ mw = 392 | 393(m$^+$H, 100%), 410(mNH$^{4+}$, 5%) DCI,NH$_3$ | CDCl$_3$ 3.65(3H, s), 3.86(3H, s), 4.25(2H, s), 6.96(2H, d), 7.02(1H, s), 7.25–7.42(8H, m). | C H N | 67.34 5.14 7.14 | 66.86 5.18 7.03 | 66.98 5.12 7.01 |
| 1499 | $C_{21}H_{18}N_2O_5$ mw = 378 | 396(mNH$^{4+}$, 8%), 379(m$^+$H, 100%) DCI-NH$_3$ | CDCl$_3$+drop TFA 3.90(3H, s), 4.40(2H, s), 7.00(2H, d), 7.21(1H, s), 7.30–7.50(8H, m). | C H N | 66.66 4.79 7.40 | 66.52 4.75 7.33 | 66.57 4.75 7.36 |
| 1817 | $C_{23}H_{22}N_2O_4$ | 408(m+NH$_4$)$^+$(5%), 391(m+H)$^+$(100%) CI,NH$_3$ | CDCl$_3$ 7.44→7.28(9H, m), 7.27(1H, s), 7.21(1H, s), 7.15(1H, s), 4.11(2H, t) 3.80(3H, t), 2.98(3H, s), 1.96(3H, s). | | | |
| 1747 | $C_{24}H_{24}N_2O_2$=388 | MH$^+$(100%)-389 Also 333, 305, 257 All < 10% DCI/NH$_3$ | 7.40–7.30(m, 7H), 7.19(s, 1H), 7.11(s, 1H), 6.92(d, 2H) 3.85(s, 3H), 3.52(d, 2H), 3.00(s, 3H), 1.01(m, 1H), 0.48(m, 2H), 0.09(m, 2H) | C H N | 74.21 6.23 7.21 | 73.95 6.24 7.15 | 74.20 6.28 7.26 |
| 1833 | $C_{24}H_{24}N_2O_3$ = 388Da | 389Da 100% DCI NH$_3$ | CDCl$_3$ 0.09(2H, m), 0.37(2H, m), 1.00(1H, m), | C H N | 74.21 6.23 7.21 | 74.20 6.95 6.57 | 74.17 6.90 6.53 |

TABLE 5-continued

| No. | Mol. Formula (M. Wt) | Mass spec m/z, mass intensity (mode) | $^1$H nmr Solvent δ all 400 MHz | Microanalysis | Calc | Found |
|---|---|---|---|---|---|---|
| | | | 3.05(3H, s), 3.49(2m, d), 3.35(3H, s), 6.42(2H, d), 7.16(2H, d), 7.27–7.40 (multiple signals solvent & sample) | | | |
| 1454 | $C_{23}H_{22}N_2O_3$ | 375(mH$^+$, 100%) DCI NH$_3$ | 0.10(2H, m), 0.39(2H, m), 1.05(1H, m), 3.58(2H, d, J=6Hț), 3.86(3H, s), 6.90(2H, d, J=7H$_z$), 7.05(1H, s), 7.20(1H, s), 7.28(2H, d, J=7H$_z$), 7.35(1H, m), 7.40(4H, m), 7.87(1H, br, s) | C H N | 73.78 5.92 7.48 | 72.95 5.94 7.42 | 73.17 5.96 7.44 |
| 1500 | $C_{23}H_{22}N_2O_3$ mw = 374 | 375(m$^+$H, 100%) DCI NH$_3$ | 0.02–0.08(2H, m), 0.43–0.47(2H, m), 0.95–1.04(1H, m), 3.55(2H, d), 3.85(3H, s), 6.98(2H, d), 7.02(1H, s), 7.22(1H, s), 7.30–7.40(7H, m), 7.94(1H, broad s). | C H N | 73.78 5.92 7.48 | 73.59 5.77 7.46 | 73.56 5.90 7.44 |
| 1780 | $C_{26}H_{28}N_2O_2$ | 401(m+H)$^+$(100%) CI,NH$_3$ | 8.08(2H, d), 7.45–7.22(9H, m), 6.85(1H, s), 4.25(2H, d), 2.98(3H, s), 2.01–1.68(6H, m) 1.40–1.09(5H, m). | C H N | 77.97 7.05 6.99 | 77.76 7.03 6.93 | 78.06 7.05 6.95 |
| 1818 | $C_{23}H_{22}N_2O_4$ | 391(m+H)$^+$(100%) CI,NH$_3$ | CDCl$_3$ 8.03(2H, d), 7.42–7.22(9H, m), 6.88(1H, s), 4.65–4.60(2H, m), 4.53→4.48(2H, m), 2.98(3H, s), 2.11(3H, s). | C H N | 70.75 5.68 7.17 | 70.37 5.75 6.99 | 70.31 5.71 6.99 |
| 1819 | $C_{22}H_{22}N_2O_3$ | 347(m+H)$^+$(100%) CI,NH$_3$ | CDCl$_3$ 8.03(2H, d), 7.40→7.18(9H, m), 6.42(1H, s), 5.12(1H, m), 3.41(3H, s), 1.04(6H, d), | C H N | 76.28 6.40 8.09 | 75.86 6.37 8.02 | 75.62 6.35 7.92 |
| 1820 | $C_{27}H_{24}N_2O_2$ | 409(m+H)$^+$ (100%) CI,NH$_3$ | CDCl$_3$ 8.08(2H, d), 7.48–7.19(14H, m), 6.82(1H, s), 4.67(2H, 5), 3.19(2H, t), 2.98(3H, s). | C H N | 79.39 5.92 6.86 | 79.23 5.90 6.83 | 79.20 5.83 6.83 |
| 1821 | $C_{23}H_{24}N_2O_2$ | 361(m+H)$^+$ 100% CI,C$_4$H$_{10}$ | CDCL$_3$ 8.08(2H, d), 7.42→7.21(9H, m), 6.88(1H, s), 4.22(2H, d), 2.98(3H, s), 2.22(1H, m), 1.11(6H, d) | | | | |
| 1822 | $C_{22}H_{24}N_2O_4$ | 405(m+H)$^+$ (100%) CI,NH$_3$ | CDCl$_3$ 8.08(2H, d), 7.42→7.21(9H, m), 6.87(1H, s), 5.13(1H, t), 4.61(2H, t), | C H N | 71.27 5.98 6.93 | 71.12 5.99 6.81 | 71.06 5.99 6.82 |

TABLE 5-continued

| No. | Mol. Formula (M. Wt) | Mass spec m/z, mass intensity (mode) | $^1$H nmr Solvent δ all 400 MHz | Microanalysis | | |
|---|---|---|---|---|---|---|
| | | | | | Calc | Found |
| | | | 4.05→3.99(2H, m) 3.93→3.86(2H, m) 2.97(3H, s), 2.26(2H, dt) | | | |
| 1824 | $C_{30}H_{25}N_3O_4$ | 492(m+H)$^+$ (100%) CI,NH$_3$ | CDCl$_3$ 8.04(2H, d), 7.87–7.78(2H, m), 7.71–7.62(2H, m), 7.45→7.23(7H, m), 7.16(2H, d), 6.80(1H, s), 4.51(2H, t), 3.96(2H, t), 2.94(3H, s), 2.30(2H, m). | | | |
| 1826 | $C_{23}H_{22}N_2O_2$ | 359(m+H)$^+$ (100%) CI,NH$_3$ | CDCl$_3$ 8.07(2H, d), 7.40→7.22(9H, m), 6.88(1H, s), 5.99→5.88(1H, sym m), 5.23(1H, d), 4.50(2H, t), 2.98(3H, s), 2.64(2H, q). | C H N | 77.07 6.19 7.82 | 76.94 76.96 6.16 6.15 7.80 7.80 |
| 1827 | $C_{21}H_{17}N_3O_2$ | 344(m+H)$^+$ (100%) CI,NH$_3$ | CDCl$_3$ 8.00(2H, d), 7.45–7.30(7H, m), 7.29→7.22(2H, m), 6.87(1H, s), 5.07(2H, s), 3.00(3H, s). | C H | 73.45 4.99 | 72.85 72.94 4.94 4.96 |
| 1855 | $C_{24}H_{26}N_2O_2$ | 375(m+H)$^+$ (100%) CI,NH$_3$ | CDCl$_3$ 8.14(2H, d), 7.40→7.20(9H, m), 6.43(1H, s), 4.12(2H, t), 3.42(3H, s), 1.46(2H, app quin), 1.37–1.28(2H, m), 0.99→0.92(2H, m), 0.81(3H, t) | | | |
| 1859 | $C_{23}H_{21}BrN_2O_2$ | 439(m+H)$^+$(15%), 437(m+H)$^+$(12%), 303(100%) CI,NH$_3$ | CDCl$_3$ 8.04(2H, d), 7.42→7.22(9H, m), 6.89(1H, s), 6.18→6.05(2H, m), 4.97(2H, d), 4.01(2H, d), 2.98(3H, s). | | | |
| 1861 | $C_{23}H_{22}N_2O_2$ | 359(m+H)$^+$(100%), 303(35%) CI,NH$_3$ | CDCl$_3$ 8.10→8.02(2H, m), 7.42→7.20(9H, m), 6.89(1H, s), 6.5.87→5.77(2H, m), 4.88(2H, d), 2.98(3H, s), 1.82→1.78(3H, m). | | | |
| 1863 | $C_{21}H_{20}N_2O_3$ | 349(mH$^+$, 100%), 304(5%) DCI NH$_3$ | CDCl$_3$ 8.02(2H, d), 7.42→7.21(9H, m), 6.41(1H, s), 4.61→4.55(2H, m), 4.10→4.03(2H, m), 2.97(3H, s), 2.12→1.91(1H, s, br) | | | |
| 1864 | $C_{22}H_{20}N_2O_2$ | 345(mH$^+$, 100%) 303(20%) DCI NH$_3$ | CDCl$_3$ 8.05(2H, d), 7.42→7.22(9H, m), 6.91(1H, s), 6.22→6.10(1H, m), 5.49(1H, d), 5.34(1H, d), 4.95(2H, d), | C H N | 76.72 5.85 8.14 | 76.77 76.62 3.82 5.83 8.14 8.14 |

TABLE 5-continued

| No. | Mol. Formula (M. Wt) | Mass spec m/z, mass intensity (mode) | ¹H nmr Solvent δ all 400 MHz | Microanalysis | | |
|---|---|---|---|---|---|---|
| | | | | | Calc | Found |
| 1771 | $C_{20}H_{18}N_2O_2 = 318$ | mH+(100%)-319 DCI/NH₃ | CDCl₃ 8.10(d, 2H), 7.42–7.30(m, 8H), 7.25(s, 1H), 6.88(s, 1H), 4.07(s, 3H), 2.99(s, 3H). | | | |
| 1801 | $C_{21}H_{20}N_2O_2$ | 333(m+H)⁺(100%) CI₆, NH₃ | CDCl₃ 8.08(2H, d), 7.42→7.22(9H, m), 6.88(1H, s), 4.51(2H, q), 2.99(3H, s), 1.51(3H, t). | | | |
| 1745 | $C_{24}H_{24}N_2O_3 = 388$ | mH⁺(100%)-389 Also, 333(20%), 305(10%), 292(10%, 257(10%). DCI,NH₃ | CDCl₃ 8.03(d, 2H), 7.37–7.27(m, 5H), 7.23 (5, 1H), 6.91(d, 2H), 6.90(s, 1H), 4.28(d, 2H), 3.85(s, 3H), 2.98(s, 3H), 1.38(m, 1H), 0.68(m, 2H), 0.43(m, 2H). | C H N | 74.21 6.23 7.21 | 73.99 6.19 7.17 | 73.95 6.22 7.18 |
| 1939 | $C_{26}H_{21}N_3O_4 = 439$ | mH⁺(100%)-440 mNH₄+(20%)-457 CI/NH₃ | CDCl₃ 8.08(d, 2H), 7.45–7.32(m, 10H), 7.26(s, 1H), 7.23(s, 1H), 7.08(d, 2H), 4.85(s, 2H), 2.98(s, 3H). | | | |
| 1936 | $C_{26}H_{21}N_3O_4 = 439$ | mH⁺(100%)-440 mNH₄⁺(60%)-457 Also-305(30%) CI/NH₃ | CDCl₃ 8.05(d, 1H), 7.70(s, 1H), 7.42–7.21(m, 14H), 4.85(s, 2H), 2.97(s, 3H) | C H N | 71.06 4.82 9.56 | 70.79 4.88 9.45 | 70.97 4.83 9.49 |
| 1906 | $C_{32}H_{26}N_2O_2$ | | CDCl₃ 7.44–7.35(m, 10H), 7.19(s, 2H), 7.18–7.07(m, 6H), 6.88(m, 4H), 4.67(4H). | C H N | 81.68 5.57 5.95 | 81.05 5.64 5.82 | 81.03 5.63 5.82 |
| 1905 | $C_{26}H_{21}N_3O_4 = 463$ | 116(25%), 160(100%), 303(30%), m⊕463(30%) Desorption chemical ionisation ammonia | CDCl₃ δ:8.08(2H, d), 7.98(2H, m), 7.85(2H, m), 7.35(9H, m), 6.78(1H, s), 6.08(2H, s), 2.95(3H, s) | | | |
| 1904 | $C_{25}H_{26}N_2O_4 = 418$ | 43(30%), 115(80%), m•418 (100%) Desorption chemical ionisation ammonia | CDCl₃ δ:1.88(2H, m), 1.95(2H, m), 2.05(3H, s), 2.98(3H, s), 4.20(2H, t), 4.45(2H, t), 6.88(1H, s), 7.35(9H, m), 8.08(2H, d). | | | |
| 1903 | $C_{31}H_{27}N_3O_4 = 505$ | 116(40%), 160(100%), 202(90%), 303(30%), m•505 (50%) Desorption chemical ionisation ammonia | CDCl₃ δ:1.95(4H, m), 2.98(3H, s), 3.85(2H, m), 4.48(2H, m), 6.88(1H, s), 7.30(9H, m), 7.80(2H, m), | C H N | 73.65 5.38 8.31 | 73.46 5.44 8.16 | 73.38 5.37 8.15 |

TABLE 5-continued

| Mol. Formula | Mass spec m/z, mass intensity | $^1$H nmr Solvent δ | Microanalysis | | |
|---|---|---|---|---|---|
| No. (M. Wt) | (mode) | all 400 MHz | | Calc | Found |
| | | 7.85(2H, m), 8.05(2H, d). | | | |
| 1902 $C_{29}H_{23}N_3O_4 = 477$ | 130(30%), 174(100%), 303(10%), mH⁺ 477 (20%) Desorption chemical ionisation ammonia | δ:8.00(2H, d), 7.80(2H, m), 7.70(2H, m), 7.35(9H, m), 6.85(1H, s), 4.68(2H, t), 4.20(2H, t), 2.98(3H, s) | C H N | 72.94 4.85 8.80 | 72.91 72.92 4.82 4.78 8.71 8.71 |
| 1901 $C_{25}H_{21}N_3O_2 = 395$ | mH⁺ 396 (100%) Desorption chemical ionisation ammonia | δ:8.45(2H, d), 7.35(10H, m), 7.26(1H, s), 7.20(1H, s), 6.85(2H, d), 4.78(2H, s), 3.00(3H, s) | | | |
| 1900 $C_{24}H_{27}N_3O_2 = 389$ | 305(50%), 376(100%), mH⁺390(70%) Desorption chemical ionisation ammonia | CDCl$_3$ δ:2.28(6H, s), 2.45(2H, t), 2.87(3H, s), 3.65(2H, t), 4.49(2H, t), 6.88(1H, s), 7.32(9H, m), 8.08(2H, d) | | | |

We claim:

1. A compound which is selected from:
(3Z,6Z)-3,6-Dibenzylidene-4-methyl-2,5-dioxo-1-piperazinylpropionaldehyde ethylene acetal; methyl-3,6-dihydro-2-pyrazinone;
(3Z,6Z)-1-Allyl-3,6-dibenzylidene-4-methyl-2,5-piperazinedione;
(3Z,6Z)-1,4-Dibenzyl-3,6-dibenzylidene-2,5-piperazinedione;
(3Z,6Z)-3,6-Dibenzylidene-1-methyl-4-(3-nitrobenzylidene)-2,5-piperazinedione;
(3Z,6Z)-1-(2-Acetoxyethyl)-3,6-dibenzylidene-4-methyl-2,5-piperazinedione;
(3Z,6Z)-3,6-Dibenzylidene-1-(2-bromoethyl)-4-methyl-2,5-piperazinedione;
(3Z,6Z)-3,6-Dibenzylidene-1-methyl-4-(4-nitrobenzylidene)-2,5-piperazinedione;
Methyl (3Z,6Z)-3-benzylidene-6-(4-methoxybenzylidene)-2,5-dioxo-1-piperazinylacetate;
N,N-Dimethyl-((3Z,6Z)-3-benzylidene-6-(4-methoxybenzylidene)-2,5-dioxo-1-piperazinyl)acetamide;
N,N-Diethyl-(3Z,6Z)-6-benzylidene-3-(4-methoxybenzylidene)-2,5-dioxo-1-piperazinylacetamide;
(3Z,6Z)-1-Benzyl-3,6-dibenzylidene-4-methyl-2,5-piperazinedione;
(3Z,6Z)-3,6-Dibenzylidene-1-(2-hydroxyethyl)-4-methyl-2,5-piperazinedione;
(3Z,6Z)-3,6-Dibenzylidene-4-methyl-1-phenethyl-2,5-piperazinedione;
(3Z,6Z)-3,6-Dibenzylidene-4-methyl-2,5-dioxo-1-piperazinylacetonitrile;
(3Z,6Z)-3,6-Dibenzylidene-1-(4-bromobut-2-enyl)-4-methyl-2,5-piperazinedione;
(3Z,6Z)-3,6-Dibenzylidene-1-(but-2-enyl)-4-methyl-2,5-piperazinedione;
(3Z,6Z)-1-Benzyl-6-(2,6-dichlorobenzylidene)-3-(4-methoxybenzylidene)-4-methyl-2,5-piperazinedione;
(3Z,6Z)-1-Benzyl-6-(4-methoxybenzylidene)-4-methyl-3-(2-nitrobenzylidene)-2,5-piperazinedione; and the pharmaceutically acceptable salts thereof.

2. A compound selected from the group consisting of a piperazine of formula (Aa):

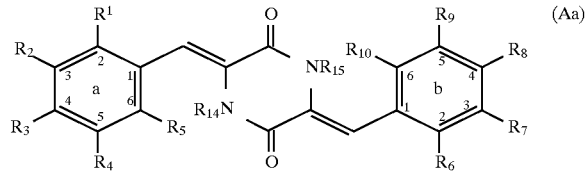

wherein each of $R_{14}$ and $R_{15}$ is independently selected from hydrogen and $C_2$–$C_6$ alkyl which is unsubstituted or substituted by a group selected from halogen, phenyl, $C_1$–$C_6$ alkenylene, cyano, hydroxy, —OC(O)R$_{11}$, —N(R$_{11}$R$_{12}$), —CON(R$_{11}$R$_{12}$), —COOR$_{11}$, a group succinimidyl, phthalimidyl or

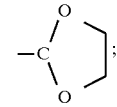

provided that at least one of $R_{14}$ and $R_{15}$ is $C_1$–$C_6$ alkyl substituted as defined above; and each of $R_1$ to $R_{10}$, which may be the same or different, is independently selected from hydrogen, $C_1$–$C_6$ alkyl unsubstituted or substituted by one or more halogen atoms, $C_1$–$C_6$ alkoxy, $C_1$–$C_6$ alkylthio, halogen, hydroxy, nitro, phenyl, cyano, —CH$_2$OH, —CH$_2$COOH, —CO$_2$R$_{11}$, —NHCOR$^{11}$, —NHSO$_2$R$^{13}$, —SO$_2$R$^{13}$, —CON(R$^{11}$R$^{12}$), —SOR$^{13}$, —SO$_2$N(R$^{11}$R$^{12}$), —N(R$^{11}$R$^{12}$), —O(CH$_2$)$_n$N(R$^{11}$R$^{12}$), —O(CH$_2$)$_n$CO$_2$R$^{11}$, —OCOR$^{11}$, —CH$_2$OCOR$^{11}$, —CH$_2$NHCOR$^{11}$, —CH$_2$NHCOOR$^{13}$, —CH$_2$SR$^{11}$, —CH$_2$SCOR$^{11}$, —CH$_2$S $(O)_mR^{13}$ wherein m is 1 or 2, $-CH_2NHCO(CH_2)_nCO_2R^{11}$, $-N(R^{11})COR^{12}$, $-NHCOCF_3$, $-NHCO(CH_2)_nCO_2R^{11}$, $-NHCO(CH_2)_nOCOR^{11}$ and $-NHCO(CH_2)_nOR^{11}$, wherein n is 0 or is an integer of from 1 to 6, each of $R^{11}$ and $R^{12}$ is independently H or $C_1-C_6$ alkyl or, when $R^{11}$ and $R^{12}$ are attached to the same nitrogen atom, they may alternatively form with the nitrogen atom an N,N-tetramethylene group; and $R^{13}$ is $C_1-C_6$ alkyl; the pharmaceutically acceptable salts thereof and the pharmaceutically acceptable esters thereof selected from the group consisting of branched and unbranched, saturated and unsaturated $C_1-C_6$ alkyl esters.

3. A compound according to claim 2 wherein one of $R_6$ to $R_{10}$ is selected from hydroxy, halogen, alkoxy, $-NHCOR^{11}$ $-CO_2R^{11}$, $-SO_2R^{13}$, $-CON(R^{11}R^{12})$, $-NO_2$, $-SO_2N(R^{11}R^{12})$, $-SOR^{13}$, and $-N(R^{11})COR^{12}$ and the other four of $R_6$ to $R_{10}$, are H.

4. A pharmaceutical or veterinary composition comprising a pharmaceutically or veterinarily acceptable carrier or diluent and, as an active principle, a compound as claimed in claim 2.

5. A process for preparing a compound as defined in claim 2, the process comprising alkylating a compound of formula (B):

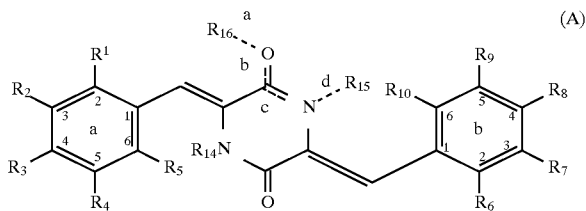

wherein $R_1$ to $R_{10}$ and $R_{14}$ are are defined in claim 2, with a compound of formula $R_{15}$—X wherein X is a halogen, in the presence of a base.

6. A method of treating resistance to an anthracycline antibiotic having neoplastic activity in a patient harboring a tumour, which method comprises administering to a patient in need thereof a therapeutically effective amount of a compound selected from the group consisting of a piperazine of formula (A):

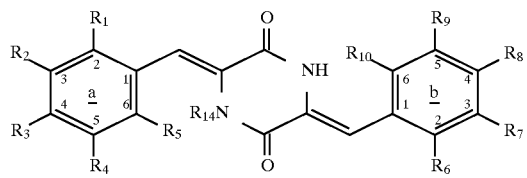

wherein _____ denotes an optional bond, provided that either ___$a$___ and ___$c$___ are both bonds and ___$b$___ and ___$d$___ are not bonds, or ___$b$___ and ___$d$___ are both bonds and ___$a$___ and ___$c$___ are not bonds;

each of $R_{14}$ and $R_{15}$ is independently selected from hydrogen and $C_1-C_6$ alkyl which is unsubstituted or substituted by a group selected from halogen, phenyl, $C_2-C_6$ alkenylene, cyano, hydroxy, $-OC(O)R_{11}$, $-N(R_{11}R_{12})$, $-CON(R_{11}R_{12})$, $-COOR_{11}$, a group succinimidyl, phthalimidyl or

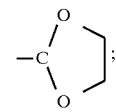

provided that when ___$b$___ and ___$d$___ are both bonds at least one of $R_{14}$ and $R_{15}$ is $C_1-C_6$ alkyl substituted as defined above; $R_{16}$ is $C_1-C_6$ alkyl unsubstituted or substituted either as defined above for $R_{14}$ and $R_{15}$ or substituted by a 4-pyridyl group; and each of $R_1$ to $R_{10}$, which may be the same or different, is independently selected from hydrogen, $C_1-C_6$ alkyl unsubstituted or substituted by one or more halogen atoms, $C_1-C_6$ alkoxy, $C_1-C_6$ alkylthio, halogen, hydroxy, nitro, phenyl, cyano, $-CH_2OH$, $-CH_2COOH$, $-CO_2R^{11}$, $-NHCOR^{11}$, $-NHSO_2R^{13}$, $-SO_2R^{13}$, $-CON(R^{11}R^{12})$, $-SOR^{13}$, $-SO_2N(R^{11}R^{12})$, $-N(R^{11}R^{12})$, $-O(CH_2)_nN(R^{11}R^{12})$, $-O(CH_2)_nCO_2R^{11}$, $-OCOR^{11}$, $-CH_2OCOR^{11}$, $-CH_2NHCOR^{11}$, $-CH_2NHCOOR^{13}$, $-CH_2SR^{11}$, $-CH_2SCOR^{11}$, $-CH_2S(O)_mR^{13}$ wherein m is 1 or 2, $-CH_2NHCO(CH_2)_nCO_2R^{11}$, $-N(R^{11})COR^{12}$, $-NHCOCF_3$, $-NHCO(CH_2)_nCO_2R^{11}$, $-NHCO(CH_2)_nOCOR^{11}$ and $-NHCO(CH_2)_nOR^{11}$; wherein n is 0 or is an integer of from 1 to 6, each of $R^{11}$ and $R^{12}$ is independently H or $C_1-C_6$ alkyl or, when $R^{11}$ and $R^{12}$ are attached to the same nitrogen atom, they may alternatively form with the nitrogen atom an N,N-tetramethylene group; and $R^{13}$ is $C_1-C_6$ alkyl; the pharmaceutically acceptable salts thereof and the pharmaceutically acceptable esters thereof selected from the group consisting of branched and unbranched, saturated and unsaturated $C_1-C_6$ alkyl esters.

7. A method of treating resistance to an anthracycline antibiotic having neoplastic activity in a patient harbouring a tumour, which method comprises administering to a patient in need thereof a therapeutically effective amount of a compound selected from the group consisting of a piperazine of formula (Aa):

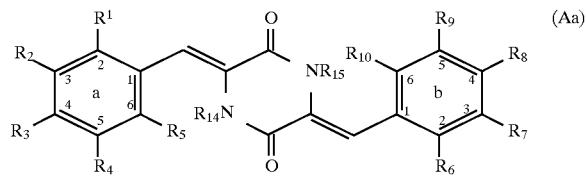

wherein each of $R_{14}$ and $R_{15}$ is independently selected from hydrogen and $C_1-C_6$ alkyl which is unsubstituted or substituted by a group selected from halogen, phenyl, optionally substituted $C_2-C_6$ alkenylene, cyano, hydroxy, $-OC(O)R_{11}$, $-N(R_{11}R_{12})$, $-CON(R_{11}R_{12})$, $-COOR_{11}$, a group succinimidyl, phthalimidyl or

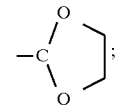

provided that at least one of $R_{14}$ and $R_{15}$ is $C_1-C_6$ alkyl substituted as defined above; and each of $R_1$ to $R_{10}$, which may be the same or different, is independently selected from hydrogen, $C_1-C_6$ alkyl unsubstituted or substituted by one or more halogen atoms, $C_1-C_6$ alkoxy, $C_1-C_6$ alkylthio, halogen, hydroxy, nitro, optionally substituted phenyl, cyano, $-CH_2OH$, $-CH_2COOH$, $-CO_2R^{11}$, $-NHCOR^{11}$, $-NHSO_2R^{13}$, $-SO_2R^{13}$, $-CON(R^{11}R^{12})$, $-SOR^{13}$, $-SO_2N(R^{11}R^{12})$, $-N(R^{11}R^{12})$, $-O(CH_2)_nN(R^{11}R^{12})$, $-O(CH_2)_nCO_2R^{11}$, $-OCOR^{11}$, $-CH_2OCOR^{11}$, —$CH_2NHCOR^{11}$, —$CH_2NHCOOR^{13}$, —$CH_2SR^{11}$, —$CH_2SCOR^{11}$, —$CH_2S(O)_mR^{13}$ wherein m is 1 or 2, —$CH_2NHCO(CH_2)_nCO_2R^{11}$, —$N(R^{11})COR^{12}$, —$NHCOCF_3$, —$NHCO(CH_2)_nCO_2R^{11}$, —$NHCO(CH_2)_nOCOR^{11}$ and —$NHCO(CH_2)_nOR^{11}$;

wherein n is 0 or is an integer of from 1 to 6, each of $R^{11}$ and $R^{12}$ is independently H or $C_1$–$C_6$ alkyl or, when $R^{11}$ and $R^{12}$ are attached to the same nitrogen atom, they may alternatively form with the nitrogen atom an N,N-tetramethylene group; and $R^{13}$ is $C_1C_6$ alkyl; the pharmaceutically acceptable salts thereof and the pharmaceutically acceptable esters thereof selected from the group consisting of branched and unbranched, saturated and unsaturated $C_1$–$C_6$ alkyl esters.

8. A method of treating resistance to an anthracycline antibiotic having a neoplastic activity in a patient harbouring a tumour, which method comprises administering to a patient in need thereof a therapeutically effective amount of a compound selected from the group consisting of a piperazine of formula (Ab):

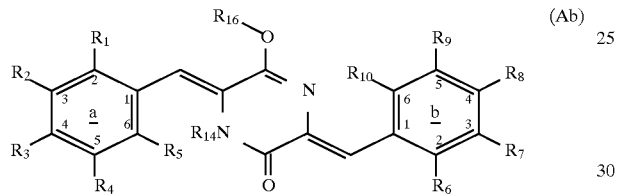
(Ab)

wherein $R_{14}$ is selected from hydrogen and $C_1$–$C_6$ alkyl which is unsubstituted or substituted by a group selected from halogen, optionally substituted phenyl, optionally substituted $C_2$–$C_6$ alkenyl, cyano, hydroxy, —$OC(O)R_{11}$, —$N(R_{11}R_{12})$, —$CON(R_{11}R_{12})$, —$COOR_{11}$, a group succinimidyl, phthalimidyl or

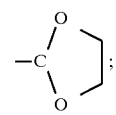

$R_{16}$ is $C_1$–$C_6$ alkyl unsubstituted or substituted either as defined above for $R_{14}$ or substituted by a 4-pyridyl group; and each of $R_1$ to $R_{10}$, which may be the same or different, is independently selected from hydrogen, $C_1$–$C_6$ alkyl unsubstituted or substituted by one or more halogen atoms, $C_1$–$C_6$ alkoxy, $C_1$–$C_6$ alkylthio, halogen, hydroxy, nitro, optionally substituted phenyl, cyano, —$CH_2OH$, —$CH_2COOH$, —$CO_2R^{11}$, —$NHCOR^{11}$, —$NHSO_2R^{13}$, —$SO_2R^{13}$, —$CON(R^{11}R^{12})$, —$SOR^{13}$, —$SO_2N(R^{11}R^{12})$, —$N(R^{11}R^{12})$, —$O(CH_2)_nN(R^{11}R^{12})$, —$O(CH_2)_nCO_2R^{11}$, —$OCOR^{11}$, —$CH_2OCOR^{11}$, —$CH_2NHCOR^{11}$, —$CH_2NHCOOR^{13}$, —$CH_2SR^{11}$, —$CH_2SCOR^{11}$, —$CH_2S(O)_mR^{13}$ wherein m is 1 or 2, —$CH_2NHCO(CH_2)_nCO_2R^{11}$, —$N(R^{11})COR^{12}$, —$NHCOCF_3$, —$NHCO(CH_2)_nCO_2R^{11}$, —$NHCO(CH_2)_nOCOR^{11}$ and —$NHCO(CH_2)_nOR^{11}$;

wherein n is 0 or is an integer of from 1 to 6, each of $R^{11}$ and $R^{12}$ is independently H or $C_1$–$C_6$ alkyl or, when $R^{11}$ and $R^{12}$ are attached to the same nitrogen atom, they may alternatively form with the nitrogen atom an N,N, tetramethylene group; and $R^{13}$ is $C_1$–$C_6$ alkyl; the pharmaceutically acceptable salts thereof and the pharmaceutically acceptable esters thereof selected from the group consisting of branched and unbranched, saturated and unsaturated $C_1$–$C_6$ alkyl esters.

9. A method according to claim 6, 7, or 8 wherein the anthracycline antibiotic is doxorubicin or daunorubicin.

10. A method according to claim 6, 7, or 8 which comprises administering the said compound to the patient whilst the tumour is exposed to the said anthracycline antibiotic.

* * * * *